United States Patent [19]
Guo et al.

[11] Patent Number: 5,783,582
[45] Date of Patent: Jul. 21, 1998

[54] PIPERIDINES AND HEXAHYDRO-1H-AZEPINES SPIRO SUBSTITUTED AT THE 4-POSITION PROMOTE RELEASE OF GROWTH HORMONE

[75] Inventors: Liangquin Guo, Fords; Arthur Patchett, Westfield; Lihu Yang, Edison, all of N.J.

[73] Assignee: Merck & Co., Inc., Rahway, N.J.

[21] Appl. No.: 776,041

[22] PCT Filed: Jul. 17, 1995

[86] PCT No.: PCT/US95/08854

§ 371 Date: Jan. 16, 1997

§ 102(e) Date: Jan. 16, 1997

[87] PCT Pub. No.: WO96/02530

PCT Pub. Date: Feb. 1, 1996

[51] Int. Cl.⁶ ............. A01N 43/42; C07D 211/00; A61K 31/44
[52] U.S. Cl. ............................. 514/278; 546/184
[58] Field of Search .................. 514/278; 546/184

[56] References Cited

U.S. PATENT DOCUMENTS 5,536,716  7/1996  Chen et al. .................. 514/212
5,578,593  11/1996  Chen et al. .................. 514/215

FOREIGN PATENT DOCUMENTS 0 144 230 A3  6/1985  European Pat. Off. .
0 513 974 A1  11/1992  European Pat. Off. .
WO 94/13696  6/1994  WIPO .

Primary Examiner—C. H. Kelly
Attorney, Agent, or Firm—J. Eric Thies; David L. Rose

[57] ABSTRACT

Di and trisubstituted Piperidines, pyrrolidines and hexahydro-1H-azepines which promote the release of growth hormone in humans and animals. This property can be utilized to promote the growth of food animals to render the production of edible mea products more efficient, and in humans, to treat physiological or medical conditions characterized by a deficiency in growth hormone secretion, such as short stature in growth hormone deficient children and to treat medical conditions which are improved by the anabolic effects of growth hormone. Growth hormone releasing compositions containing such di- and trisubstituted piperidines and pyrrolidines as the active ingredient thereof are also disclosed.

16 Claims, No Drawings

PIPERIDINES AND HEXAHYDRO-1H-AZEPINES SPIRO SUBSTITUTED AT THE 4-POSITION PROMOTE RELEASE OF GROWTH HORMONE

This application is a 371 of PCT/US/95/08,854.

BACKGROUND OF THE INVENTION

Growth hormone, which is secreted from the pituitary, stimulates growth of all tissues of the body that are capable of growing In addition, growth hormone is known to have the following basic effects on the metabolic processes of the body:

1. Increased rate of protein synthesis in all cells of the body;
2. Decreased rate of carbohydrate utilization in cells of the body;
3. Increased mobilization of free fatty acids and use of fatty acids for energy.

A deficiency in growth hormone secretion can result in various medical disorders, such as dwarfism.

Various ways are known to release growth hormone. For example, chemicals such as arginine, L-3,4-dihydroxyphenylalanine (L-DOPA), glucagon, vasopressin, and insulin induced hypoglycemia, as well as activities such as sleep and exercise, indirectly cause growth hormone to be released from the pituitary by acting in some fashion on the hypothalamus perhaps either to decrease somatostatin secretion or to increase the secretion of the known secretagogue growth hormone releasing factor (GRF) or an unknown endogenous growth hormone-releasing hormone or all of these.

In cases where increased levels of growth hormone were desired, the problem was generally solved by providing exogenous growth hormone or by administering an agent which stimulated growth hormone production and/or release. In either case the peptidyl nature of the compound necessitated that it be administered by injection. Initially the source of growth hormone was the extraction of the pituitary glands of cadavers. This resulted in a very expensive product and carried with it the risk that a disease associated with the source of the pituitary gland could be transmitted to the recipient of the growth hormone. Recently, recombinant growth hormone has become available which, while no longer carrying any risk of disease transmission, is still a very expensive product which must be given by injection or by a nasal spray.

Other compounds have been developed which stimulate the release of endogenous growth hormone such as analogous peptidyl compounds related to GRF or the peptides of U.S. Pat. No. 4,411,890. These peptides, while considerably smaller than growth hormones are still susceptible to various proteases. As with most peptides, their potential for oral bioavailability is low. Non peptidal growth hormone secretagogues with a benzo-lactam structure are disclosed in U.S. Pat. No. 4,206,235. The instant compounds are non-peptide analogs for promoting the release of growth hormone which are stable in a variety of physiological environments and which may be administered parenterally, nasally or by the oral route.

SUMMARY OF THE INVENTION

The instant invention covers certain piperidine and hexahydro-1H-azepine compounds spiro substituted at the 4-position which have the ability to stimulate the release of natural or endogenous growth hormone. The compounds thus have the ability to be used to treat conditions which require the stimulation of growth hormone production or secretion such as in humans with a deficiency of natural growth hormone or in animals used for food or wool production where the stimulation of growth hormone will result in a larger, more productive animal. Thus, it is an object of the instant invention to describe the piperidine and hexahydro-1H-azepine compounds spiro substituted at the 4-position. It is a further object of this invention to describe procedures for the preparation of such compounds. A still further object is to describe the use of such compounds to increase the secretion of growth hormone in humans and animals. A still further object of this invention is to describe compositions containing the piperidine and hexahydro-1H-azepine compounds spiro substituted at the 4-position for the use of treating humans and animals so as to increase the level of growth hormone secretions. Further objects will become apparent from a reading of the following description.

DESCRIPTION OF THE INVENTION

The novel 4-spiro piperidines and hexahydro-1H-azepines of the instant invention are best described in the following structural formula I:

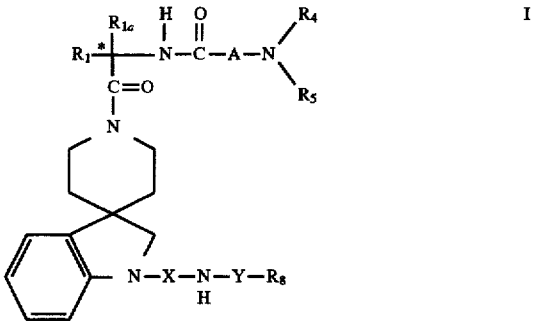

wherein:

$R_1$ is selected from the group consisting of:

$C_1$–$C_{10}$ alkyl-, aryl-, aryl($C_1$–$C_6$ alkyl)-, heteroaryl-, heteroaryl($C_1$–$C_6$ alkyl)-, ($C_3$–$C_7$ cycloalkyl)-($C_1$–$C_6$ alkyl)-, ($C_1$–$C_5$ alkyl)-K-($C_1$–$C_5$ alkyl)-, aryl-($C_0$–$C_5$ alkyl) -K-($C_1$–$C_5$ alkyl)-, heteroaryl-($C_0$–$C_5$ alkyl)-K-($C_1$–$C_5$ alkyl)-, and ($C_3$–$C_7$ cycloalkyl)-($C_0$–$C_5$ alkyl)-K-($C_1$–$C_5$ alkyl)-, wherein K is —O—, —S(O)$_m$—, —N($R_2$)C(O)—, —C(O)N($R_2$)—, —OC(O)—, —C(O)O—, —CR$_2$=CR$_2$— or —C≡C—, wherein $R_2$ and the alkyl groups are optionally further substituted with 1 to 9 halo, —S(O)$_m R_{2a}$, 1 to 3 of —OR$_{2a}$, or —C(O)OR$_{2a}$, and wherein aryl is phenyl or naphthyl, and heteroaryl is selected from indolyl, thiopheneyl, furanyl, benzothiopheneyl, benzofuranyl, pyridinyl, quinolinyl, triazolyl, imidazolyl, thiazolyl, and benzimidazolyl, wherein aryl and heteroaryl are unsubstituted or substituted with phenyl, phenoxy, halophenyl, 1 to 3 of —$C_1$–$C_6$ alkyl, 1 to 3 of halo, 1 to 2 of —OR$_2$, methylenedioxy, —S(O)$_m R_2$, 1 to 2 of —CF$_3$, —OCF$_3$, nitro, —N($R_2$)($R_2$), —N($R_2$)C(O) ($R_2$), —C(O)OR$_2$, —C(O)N($R_2$)($R_2$), —SO$_2$N($R_2$)($R_2$), —N($R_2$)SO$_2$-aryl, or —N($R_2$)SO$_2R_2$;

$R_{1a}$ is hydrogen or $C_1$–$C_4$ alkyl;

$R_2$ is selected from the group consisting of: hydrogen, —$C_1$–$C_6$ alkyl, —$C_3$–$C_7$ cycloalkyl, and —CH$_2$-phenyl, wherein the alkyl or the cycloalkyl is unsubstituted or substituted with hydroxyl, $C_1$–$C_3$ alkoxy, thioalkyl, C(O)OR$_{2a}$, and wherein, if two —$C_1$–$C_6$ alkyl groups are present on one atom, the groups are optionally joined to form a $C_3$–$C_8$ cyclic ring optionally including oxygen, sulfur, or $NR_{2a}$, the $C_3$–$C_8$ cyclic ring being selected from the group consisting of pyrrolidine, piperidine, piperazine, morpholine, and thiomorpholine;

$R_{2a}$ is hydrogen or $C_1$–$C_6$ alkyl;

$R_4$ and $R_5$ are independently selected from the group consisting of: hydrogen, $C_1$–$C_6$ alkyl, substituted $C_1$–$C_6$ alkyl where the substituents are selected from: 1 to 5 halo, 1 to 3 hydroxy, 1 to 3 $C_1$–$C_{10}$ alkanoyloxy, 1 to 3 $C_1$–$C_6$ alkoxy, phenyl, phenoxy, 2-furyl, $C_1$–$C_6$ alkoxycarbonyl, and —$S(O)_m(C_1$–$C_6$ alkyl); or wherein $R_4$ and $R_5$ may be taken together to form —$(CH_2)_rL_a(CH_2)_s$—, wherein $L_a$ is —$C(R_2)_2$—, —O—, —$S(O)_m$— or —$N(R_2)$—, wherein r and s are independently 1 to 3, and $R_2$ is defined above;

A is:

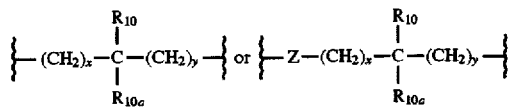

wherein x and y are independently 0, 1, 2 or 3;

Z is —$N(R_9)$— or —O—, wherein $R_9$ is hydrogen or $C_1$–$C_6$ alkyl;

$R_{10}$ and $R_{10a}$ are independently selected from the group consisting of: hydrogen, —$C_1$–$C_6$ alkyl, trifluoromethyl, phenyl, and substituted $C_1$–$C_6$ alkyl wherein the substituents are selected from the group consisting of: imidazolyl, phenyl, indolyl, naphthyl, p-hydroxyphenyl, —$OR_2$, —$S(O)_mR_2$, —$C(O)OR_2$, —$C_3$–$C_7$ cycloalkyl, —$N(R_2)(R_2)$, and —$C(O)N(R_2)(R_2)$;

or $R_{10}$ and $R_{10a}$ are independently joined to one or both of $R_4$ and $R_5$ groups to form an alkylene bridge between the terminal nitrogen and the alkyl portion of the $R_{10}$ or $R_{10a}$ groups, wherein the bridge contains 1 to 5 carbons atoms;

$R_8$ is hydrogen, $C_1$–$C_{10}$ alkyl, phenyl, benzyl or diphenyl methyl wherein the phenyl, benzyl or diphenyl groups may be substituted by halo, methyl or $OR_2$;

X is $SO_2$ or CO; and

Y is selected from a chemical bond, $SO_2$, CO, C(O)O, $C(O)N(R_2)$, and $SO_2N(R_2)$;

m is 0, 1, or 2; and n is 1 or 2;

and pharmaceutically acceptable salts and individual diastereomers thereof.

In the above structural formula and throughout the instant specification, the following terms have the indicated meanings:

The alkyl groups specified above are intended to include those alkyl groups of the designated length in either a straight or branched configuration which may optionally contain double or triple bonds. Exemplary of such alkyl groups are methyl, ethyl, propyl, isopropyl, butyl, sec-butyl, tertiary butyl, pentyl, isopentyl, hexyl, isohexyl, allyl, propinyl, butadienyl, hexenyl and the like.

The alkoxy groups specified above are intended to include those alkoxy groups of the designated length in either a straight or branched configuration which may optionally contain double or triple bonds. Exemplary of such alkoxy groups are methoxy, ethoxy, propoxy, isopropoxy, butoxy, isobutoxy, tertiary butoxy, pentoxy, isopentoxy, hexoxy, isohexoxy, allyloxy, propinyloxy, isobutenyloxy, hexenyloxy and the like.

The term "halo" or "halogen" is intended to include the halogen atoms fluorine, chlorine, bromine and iodine.

The term "aryl" (unless otherwise specified) is intended to include phenyl and naphthyl. The term "heteroaryl" (unless otherwise specified) is intended to include aromatic residues of 5- and 6- membered rings with 1 to 3 heteroatoms or fused 5- or 6- membered bicyclic rings with 1 to 4 heteroatoms of nitrogen, sulfur or oxygen. Examples of such heteroaryl include indolyl, dihydroindolyl, thiophenyl, furanyl, benzothiopheneyl, benzofuranyl, pyridinyl, pyrimidinyl, quinolinyl, triazolyl, imidazolyl, thiazolyl, tetrazolyl, and benzimidazolyl.

Certain of the above defined terms may occur more than once in the above formula and upon such occurrence each term shall be defined independently of the other, i.e. when any variable (e.g., alkyl, aryl, $R_2$, etc.) occurs more than one time within any variable or in Formula I, its definition on each occurrence is independent of its definition at every other occurrence.

Preferred compounds of the instant invention include those of structural formula I wherein:

$R_1$ is selected from the group consisting of: $C_1$–$C_{10}$ alkyl, aryl($C_1$–$C_4$ alkyl)-, $C_5$–$C_6$ cycloalkyl-($C_1$–$C_4$ alkyl)-, ($C_1$–$C_4$ alkyl)-K—$C_1$–$C_2$ alkyl-, aryl($C_0$–$C_2$ alkyl)-K-($C_1$–$C_2$ alkyl)-, $C_3$–$C_6$cycloalkyl($C_0$–$C_2$alkyl)-K-($C_1$–$C_2$alkyl)-, wherein K is O or $S(O)_m$, and the aryl is phenyl, or naphthyl and the heteroaryl is indolyl and the aryl and heteroaryl groups are optionally unsubstituted or substituted by 1 to 2 $C_1$–$C_4$ alkyl, 1 to 2 halo, $OR_2$, $C(O)OR_2$, $CF_3$ or $S(O)_mR_2$;

$R_2$ is selected from the group consisting of: hydrogen, $C_1$–$C_6$ alkyl, $C_3$–$C_6$ cycloalkyl, wherein the alkyl or the cycloalkyl is unsubstituted or substituted with hydroxyl, $C_1$–$C_3$ alkoxy, thioalkyl, $C(O)OR_{2a}$, and, if two $C_1$–$C_6$ alkyls are present on one atom, they may be optionally joined to form a $C_5$–$C_6$ cyclic ring optionally including the heteroatoms oxygen or $NR_{2a}$, the $C_3$–$C_8$ cyclic ring being selected from the group consisting of pyrrolidine, piperidine, piperazine, morpholine, thiomorpholine;

$R_{2a}$ is hydrogen or $C_1$–$C_4$ alkyl;

$R_4$ and $R_5$ are independently selected from the group consisting of: hydrogen, $C_1$–$C_4$ alkyl, substituted $C_1$–$C_4$ alkyl where the substituents are 1 to 2 hydroxy or $S(O)_m(C_1$–$C_3$alkyl); or wherein $R_4$ and $R_5$ are optionally taken together to form $(CH_2)_rN(R_2)(CH_2)_s$ wherein r and s are independently 1 to 3 and $R_2$ is defined above;

A is:

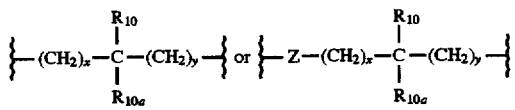

wherein x and y are independently 0,1 or 2;

Z is —$N(R_9)$— or —O—, wherein $R_9$ is hydrogen or $C_1$–$C_4$ alkyl;

$R_{10}$ and $R_{10a}$ are independently selected from the group consisting of: hydrogen, $C_1$–$C_3$ alkyl; or $R_{10}$ and $R_{10a}$ are optionally independently joined to one or both of the $R_4$ and $R_5$ groups to form an alkylene bridge between the terminal nitrogen and the alkyl portion of the $R_{10}$ or $R_{10a}$ groups to form 5 or 6 membered rings containing the terminal nitrogen;

X is $SO_2$;
Y is CO, C)$_2$, or $SO_2$;
$R_8$ is $C_1$–$C_6$ alkyl, phenyl or benzyl optionally substituted with halo, methyl or $OR_2$;
m is 0, 1, or 2; and
n is 1;

or their pharmaceutically acceptable salts and individual diastereomers thereof.

Most preferred compounds of the instant invention are realized in structural formula V:

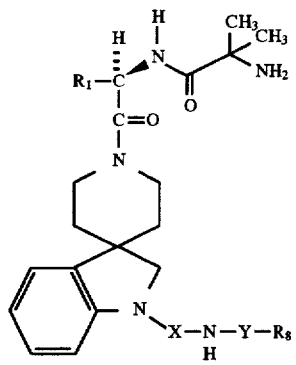

V wherein $R_1$ is selected from the group consisting of:

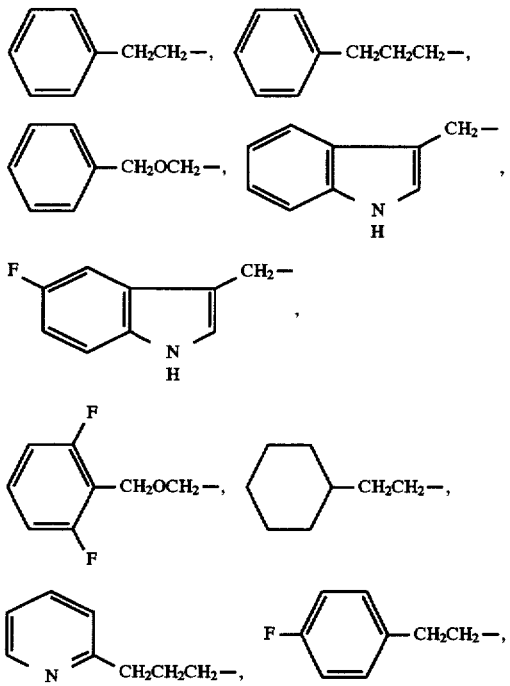

and

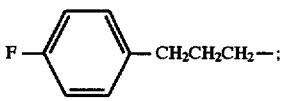

$R_2$ is selected from the group consisting of: hydrogen, $C_1$–$C_4$ alkyl;

$R_4$ and $R_5$ are independently selected from the group consisting of hydrogen, $C_1$–$C_4$ alkyl, substituted $C_1$–$C_4$ alkyl wherein the substituents are 1 to 2 hydroxy or wherein $R_4$ and $R_5$ are optionally taken together to form piperazine;

A is

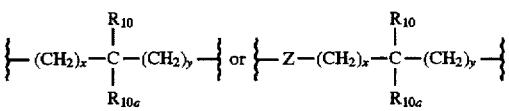

wherein x and y are independently 0, 1 or 2;

Z is $N(R_9)$ or —O—, wherein $R_9$ is hydrogen or methyl;

$R_{10}$ and $R_{10a}$ are independently selected from the group consisting of hydrogen and $C_1$–$C_3$ alkyl; or $R_{10}$ and $R_{10a}$ are optionally independently joined to one or both of the $R_4$ and $R_5$ group to form pyrrolidine or piperidine rings;

X is $SO_2$;

Y is CO or $SO_2$;

$R_8$ is hydrogen, $C_1$–$C_4$ alkyl, phenyl or benzyl optionally substituted by halo, methyl or $OR_2$; and m is 0, 1, or 2;

and the pharmaceutically acceptable salts and individual diastereomers 10 thereof.

Representative most preferred growth hormone releasing compounds of the present invention include the following:

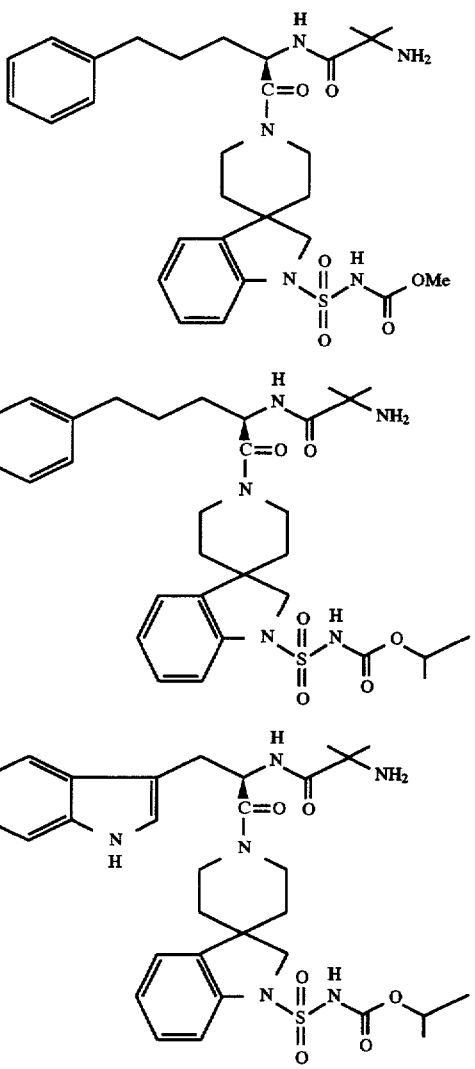

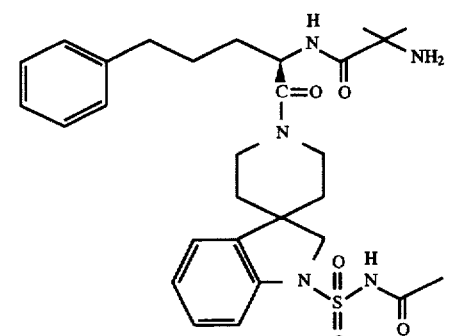
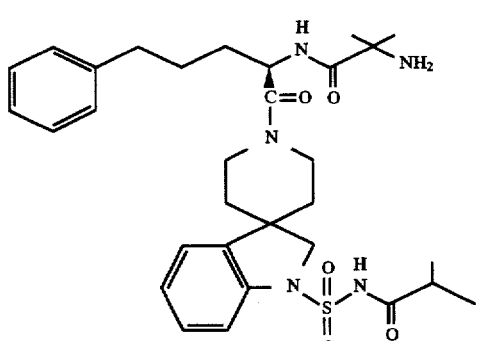
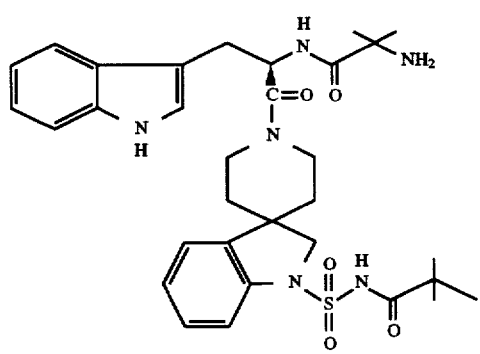
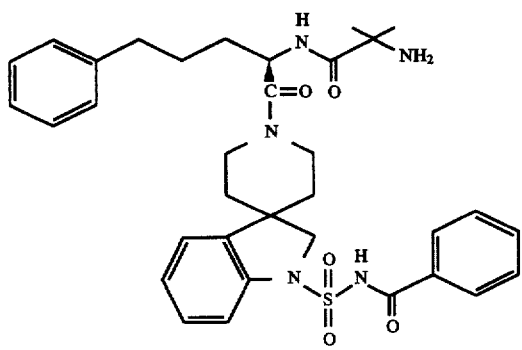
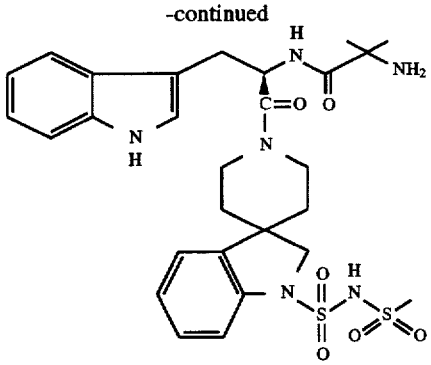
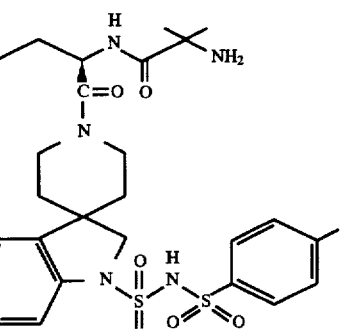
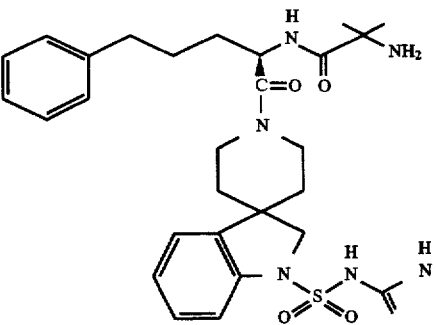

or a pharmaceutically acceptable salt thereof.

Throughout the instant application, the following abbreviations are used with the following meanings:

| | |
|---|---|
| BOC | t-butyloxycarbonyl |
| BOP | Benzotriazol-1-yloxy tris(dimethylamino)-phosphonium hexafluorophosphate |
| CBZ | Benzyloxycarbonyl |
| DIBAL-H | diisobutylaluminum hydride |
| DMF | N,N-dimethylformamide |
| EDC | 1-(3-dimethylaminopropyl)-3-ethylcarbodiimide hydrochloride |
| FAB-MS | Fast atom bombardment-mass spectroscopy |
| GHRP | Growth hormone releasing peptide |
| HOBT | Hydroxybenztriazole |
| LAH | Lithium aluminum hydride |
| HPLC | High pressure liquid chromatography |
| MHz | Megahertz |
| MPLC | Medium pressure liquid chromatography |
| NMM | N-Methylmorpholine |
| NMR | Nuclear Magnetic Resonance |
| TFA | Trifluoroacetic acid |
| THF | Tetrahydrofuran |
| TLC | Thin layer chromatography |
| TMS | Tetramethylsilane |

The compounds of the instant invention all have at least one asymmetric center as noted by the asterisk in the structural Formula I above. Additional asymmetric centers may be present on the molecule depending upon the nature of the various substituents on the molecule. Each such asymmetric center will produce two optical isomers and it is intended that all such optical isomers, as separated, pure or partially purified optical isomers, racemic mixtures or diastereomeric mixtures thereof, be included within the ambit of the instant invention. In the case of the asymmetric center represented by the asterisk in Formula I, it has been found that the absolute stereochemistry of the more active and thus more preferred isomer is as shown in Formula II in which $R_{2a}$ is represented by a hydrogen. With the $R_{1a}$ substituent as hydrogen, the special configuration of the asymmetric center corresponds to that in a D-amino acid. In most cases this is also designated an R-configuration although this will vary according to the values of $R_1$ and $R_{1a}$ used in making R- or S- stereochemical assignments.

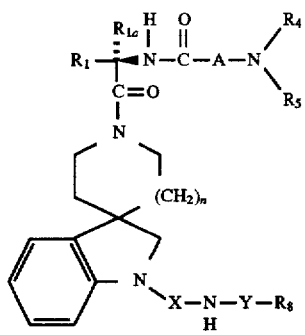

Formula II

The instant compounds are generally isolated in the form of their pharmaceutically acceptable acid addition salts, such as the salts derived from using inorganic and organic acids. Examples of such acids are hydrochloric, nitric, sulfuric, phosphoric, formic, acetic, trifluoroacetic, propionic, maleic, succinic, malonic, methane sulfonic and the like. In addition, certain compounds containing an acidic function such as a carboxy may be isolated in the form of their inorganic salt in which the counterion may be selected from sodium, potassium, lithium, calcium, magnesium and the like, as well as from organic bases.

The preparation of compounds of Formula I of the present invention may be carried out in sequential or convergent synthetic routes. Syntheses detailing the preparation of the compounds of Formula I in a sequential manner are presented in the following reaction schemes in which $R_{2a}$ is shown as H.

The phrase "standard peptide coupling reaction conditions" is used repeatedly here, and it means coupling a carboxylic acid with an amine using an acid activating agent such as EDC, DCC, and BOP in a inert solvent such as dichloromethane in the presence of a catalyst such as HOBT. The uses of protective groups for amine and carboxylic acid to facilitate the desired reaction and minimize the undesired reaction are well documented. Conditions required to remove protecting groups which may be present and can be found in Greene, T; Wuts, P. G. M. *Protective Groups in Organic Synthesis*, John Wiley & Sons, Inc., New York, N.Y. 1991. CBZ and BOC were used extensively in the synthesis, and their removal conditions are known to those skilled in the art. Removal of CBZ groups may be achieved by a number of methods known in the art; for example, catalytic hydrogenation with hydrogen in the presence of a nobel metal or its oxide such as palladium on activated carbon in a protic solvent such as ethanol. In cases where catalytic hydrogenation is contraindicated by the presence of other potentially reactive functionality, removal of CBZ groups may also be achieved by treatment with a solution of hydrogen bromide in acetic acid, or by treatment with a mixture of TFA and dimethylsulfide. Removal of BOC protecting groups is carried out in a solvent such as methylene chloride or methanol or ethyl acetate, with a strong acid, such as trifluoroacetic acid or hydrochloric acid or hydrogen chloride gas.

The protected amino acid derivatives 1 are, in many cases, commercially available, where the protecting group L is, for example, BOC or CBZ groups. Other protected amino acid derivatives 1 may be prepared by literature methods (Williams, R. M. *Synthesis of Optically Active a-Amino Acids*, Pergamon Press: Oxford, 1989). Many of the piperazines of formula 2 are either commercially available or known in the literature and others may be prepared following literature methods described for known compounds, some of which are described here. The skills required in carrying out the reaction and purification of the resulting reaction products are known to those in the art. Purification procedures includes crystallization, normal phase or reverse phase chromatography.

SCHEME 1

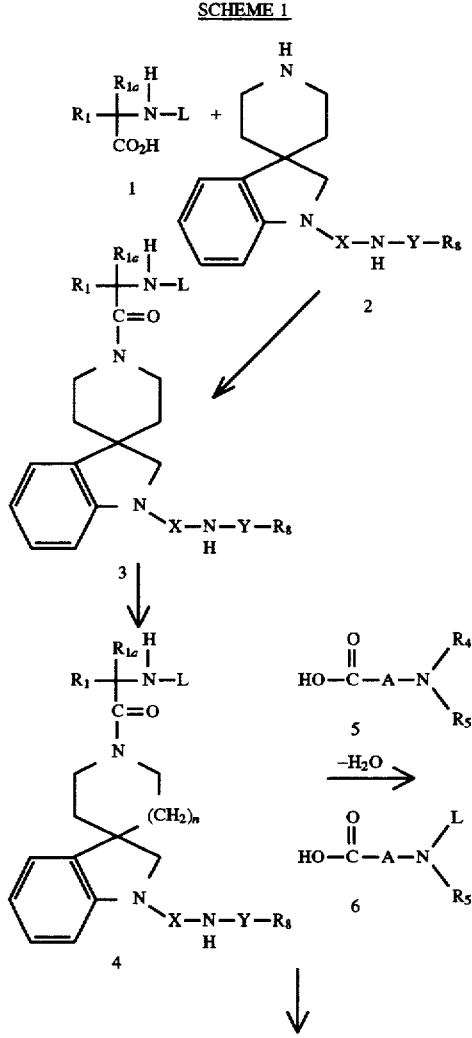

-continued
SCHEME 1

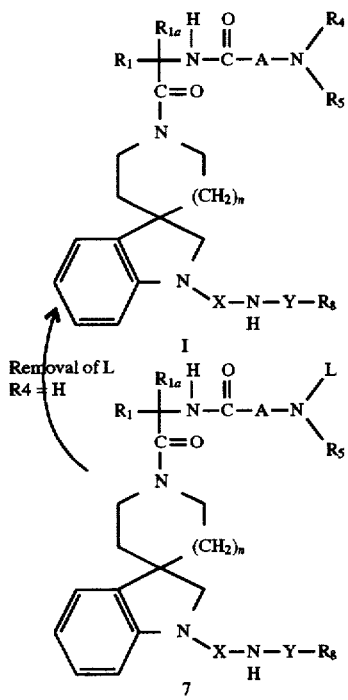

Coupling of the protected amino acids of formula 1, wherein L is a suitable protecting group, with amine of formula 2, whose preparations are described later, where X, Y and $R_8$ are as defined above, is conveniently carried out under standard peptide coupling conditions to give intermediates of formula 3 as illustrated in Scheme 1. Conversion of 3 to intermediate 4 can be carried out as illustrated in the scheme by removal of the protecting group L (CBZ, BOC, etc.). Intermediates of formula 5, wherein A is connected to the carbonyl by a carbon atom and thus A is —$(CH2)_x$—C$(R7)(R7_a)$—$(CH2)_y$— can be prepared as shown in Scheme 1 by coupling intermediates of formula 4 to amino acids of formula 5 under the standard peptide coupling reaction conditions. The amino acids 5, as amino acid 1, are either commercially available or can be synthesized. Also if $R_4$ or $R_5$ is a hydrogen then the protected amino acids 6 are employed in the coupling reaction, wherein L is a protecting group as defined above. The removal of L in 7 to afford 1, where $R_4$=H, can be carried out under conditions known in the art.

SCHEME 2

-continued
SCHEME 2

Compounds of formula I wherein $R_4$ and/or $R_5$ is a hydrogen can be further elaborated to new compounds I (with preferred side chains $R_4$=$CH_2$—CH(OH)—$CH_2$X, wherein X=H or OH) which are substituted on the amino group as depicted in Scheme 2. Reductive alkylation of 1 with an aldehyde is carried out under conditions known in the art; for example, by catalytic hydrogenation with hydrogen in the presence of platinum, palladium, or nickel catalysts or with chemical reducing agents such as sodium cyanoborohydride in a protic solvent such as methanol or ethanol in the present of catalytic amount of acid. Alternatively, a similar transformation can be accomplished via an epoxide opening reaction.

SCHEME 3

Compounds of formula I, wherein A is Z—$(CH_2)_x$—C$(R_7)(R_{7a})$—$(CH_2)_y$, and Z is N—$R_6$ or O can be prepared as shown in Scheme 3 by reacting 4 with reagents 8, wherein X is a good leaving group such as Cl, Br, I, or imidazole. Alternatively, 4 can be reacted with an isocyanate of formula 9 in an inert solvent such as 1,2-dichloroethane to provide compounds of formula I where Z is NH.

The compounds of general formula I of the present invention can also be prepared in a convergent manner as described in reaction Schemes 4, 5 and 6.

The carboxylic acid protected amino acid derivatives 10 are, in many cases, commercially available where M=methyl, ethyl, or benzyl esters. Other ester protected amino acids can be prepared by classical methods familiar to those skilled in the art. Some of these methods include the reaction of the amino acid with an alcohol in the presence of an acid such as hydrochloric acid or p-toluenesulfonic acid and azeotropic removal of water. Other syntheses include the reaction of a protected amino acid with a diazoalkane, or with an alcohol and an acid activating agent such as EDC, DCC in the presence of a catalyst such as DMAP and removal of the protecting group L.

SCHEME 4

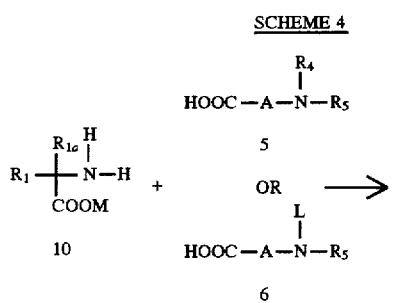

Intermediates of formula 11 or 11a, can be prepared as shown in Scheme 4 by coupling of amino acid ester 10 to amino acids of formula 6 or 7. When a urea or carbamate linkage is present in 11 or 11a, it can be introduced as illustrated in Scheme 3.

SCHCME 5

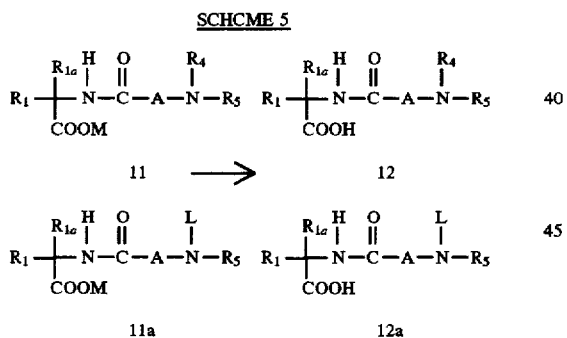

Conversion of the ester 11 or 11a to intermediate acids 12 or 12a can be achieved by a number of methods known in the art as described in Scheme 5; for example, methyl and ethyl esters can be hydrolyzed with lithium hydroxide in a protic solvent like aqueous methanol. In addition, removal of benzyl group can be accomplished by a number of reductive methods including hydrogenation in the presence of palladium catalyst in a protic solvent such as methanol. An allyl ester can be cleaved with tetrakistriphenylphoshine palladium catalyst in the presence of 2-ethylhexanoic acid in a variety of solvents including ethyl acetate and dichloromethane (see *J. Org. Chem.* 1982, 42, 587).

SCHEME 6

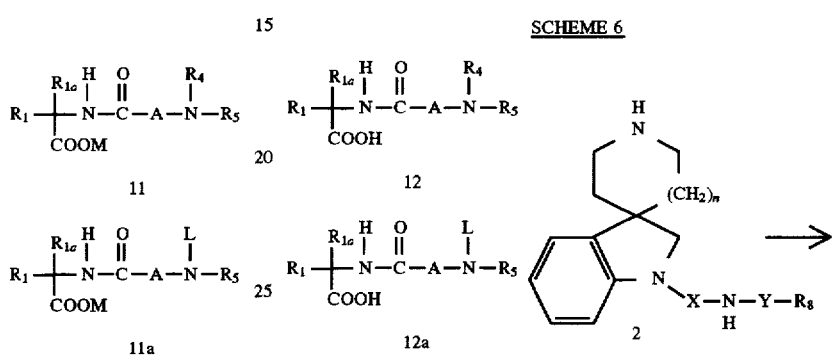

Acid 12 or 12a can then be elaborated to I or compound 7 as described in Scheme 6. Coupling of compounds of formula 2 to acids of formula 12 or 12a, wherein L is a suitable protecting group, is conveniently carried out under the standard peptide coupling reaction conditions. Transformation of 7 to I is achieved by removal of the protecting group L. When $R_4$ and/or $R_5$ is H, substituted alkyl groups may be optionally added to the nitrogen atom as described in Scheme 4.

SCHEME 7

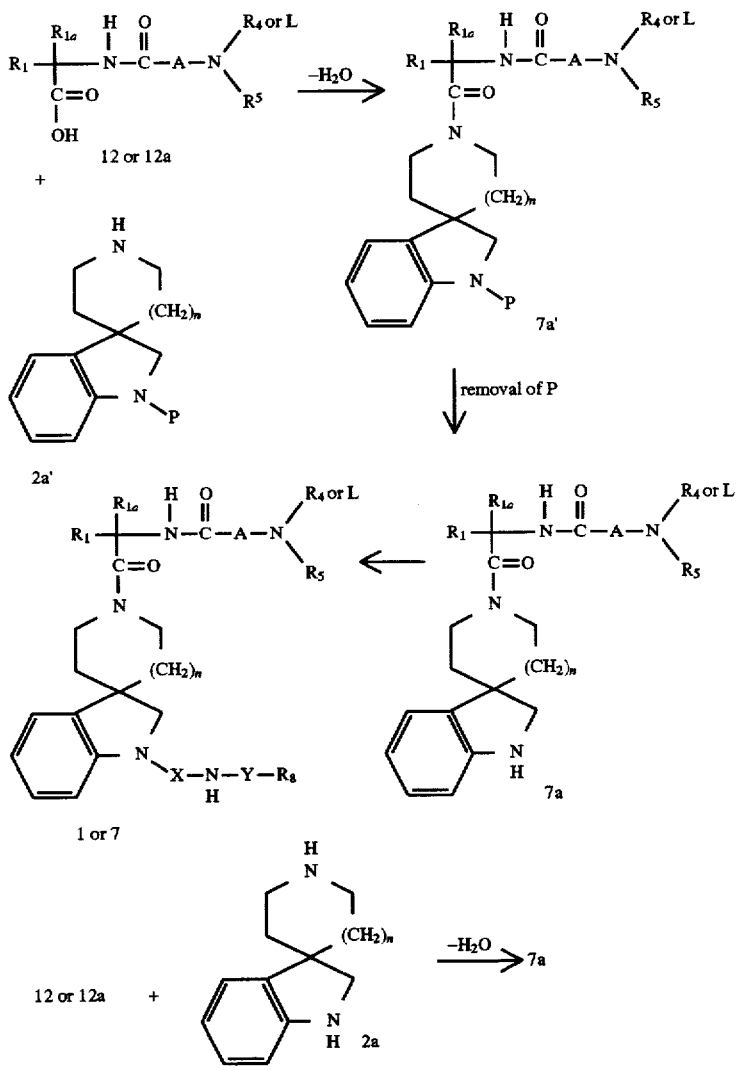

An alternative way of preparing compounds of structure I can be achieved through coupling reaction of 12 or 12a with spiroindoline 2a' (H. Ong et al *J. Med. Chem.* 1983, 23, 981–986), with P is a protecting group, under the standard peptide coupling reactions. Then, removal of the protecting group at the indoline nitrogen and the functionalities attached to this position can be introduced according to the established procedures some of which are described later in this patent. Alternatively, compounds 12 or 12a can be coupled directly with the unprotected spiroindoline 2a selectively at the piperidine position to yield compound 7a.

SCHEME 8
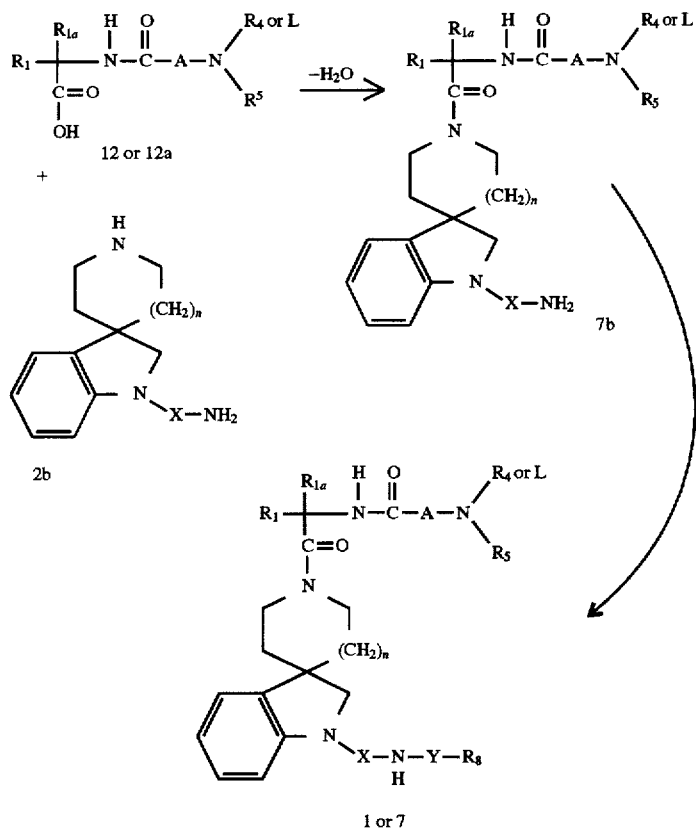
Alternatively, the acid 12 or 12a can be coupled to the spirocompounds 2b under the standard peptide coupling to give intermediates 7b, which could be further elaborated to yield compound I or 7 under conditions described later.
SCHEME 9
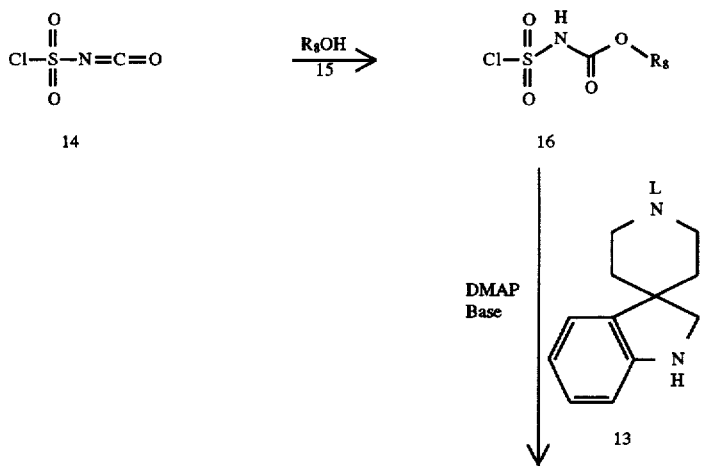

-continued
SCHEME 9

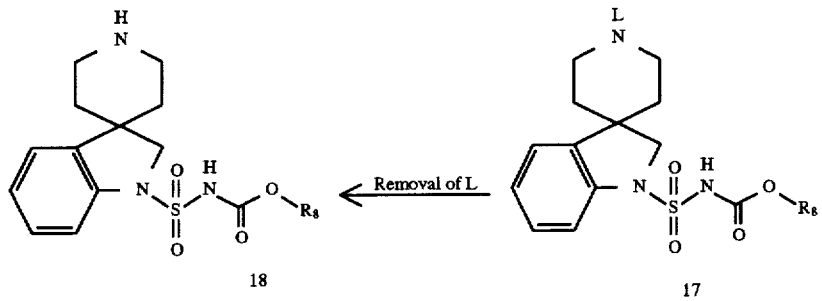

The spiroindolines 13, where L is a protecting group such as CBZ, BOC can be prepared by procedures known in the literature (for example H. Ong et al *J. Med. Chem.* 1983, 23, 981–986). The reaction between chlorosulfonyl isocyanate and an alcohol 15, where $R_8$ is defined as above, to give a (chlorosulfonyl) carbamate 16 is well documented (see Burgess et al *Organic Systeses vol.* VI, 788). Treatment of the spiroindoline 13 with the (chlorosulfonyl) carbamate 16 in the present of a base such as triethylamine or NMM and a catalyst such as DMAP gives the alkyl carboxysulfamide 17. Removal of the protective group L under appropriate conditions affords the piperidine compound 18, an example of compounds of general formula 2.

SCHEME 10

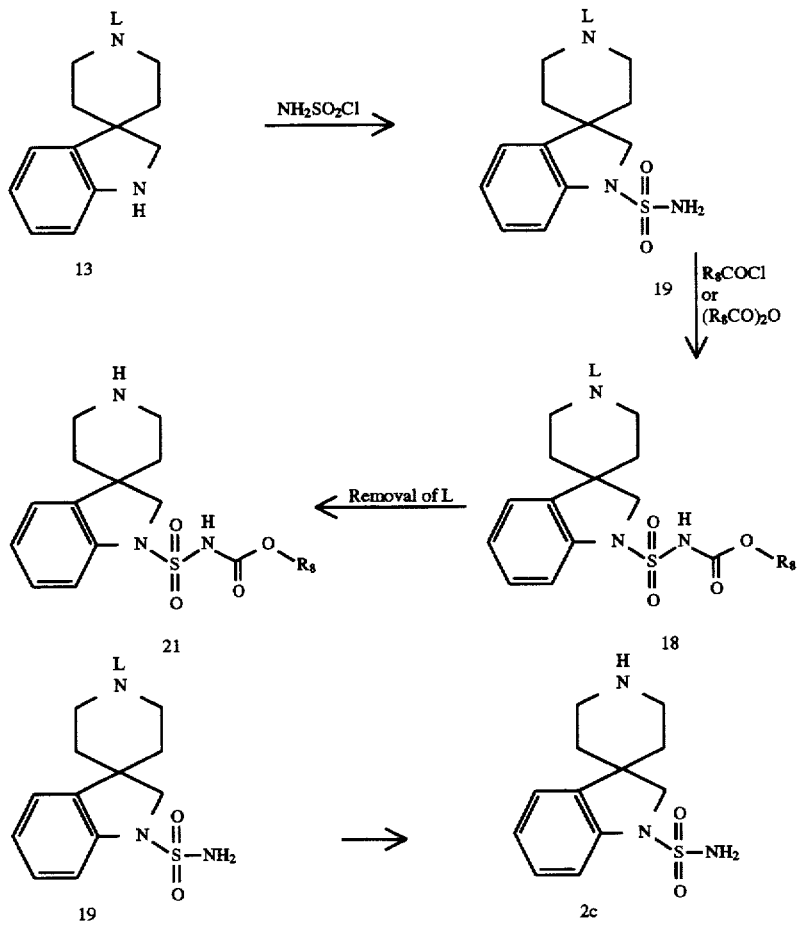

As shown in Scheme 10, reaction of the indoline 13 with chlorosulfamide (*J. Org. Chem.* 54, 5825, 1989) in the presence of a base such as NMM gives the sulfamide 19. Acylation of the resulting sulfamide 19 with acyl chloride or anhydride in the presence of base such as triethylamine or NMM and catalytic amount of DMAP gives the acyl sulfamide 20. The acyl sulfamide 20 can also be prepared by reaction of 19 with a carboxylic acid $R_8CO_2H$ in the presence of a carboxylic acid activating reagent such as EDC, DCC and a catalyst such as DMAP. It is noted that the reaction described here can be also used in the advanced intermediates 7a shown in Scheme 7.

Removal of the protecting group L gives compound 21, an example of compounds of general formula 2. Removal of L in compound 19 gives piperidine 2c, an example of compound 2b (Scheme 8).

SCHEME 11

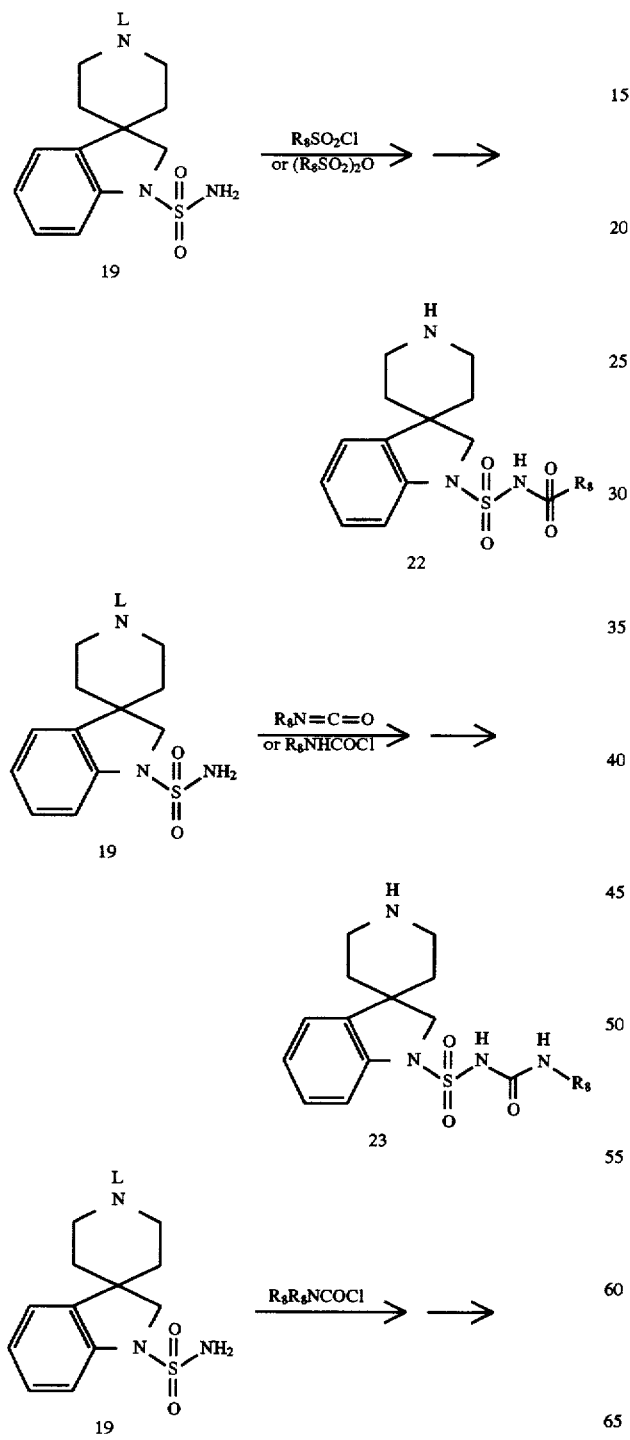

-continued
SCHEME 11

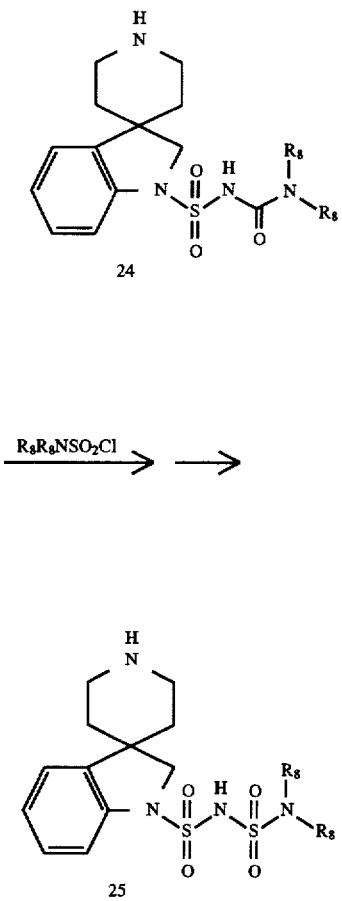

As shown in Scheme 11, the sulfonyl sulfamide 22 can be prepared similarly by reaction of compound 19 with a sulfonyl chloride or sulfonyl anhydride followed by removal of L. The carbamyl sulfamide 23, 24 can be prepared by reaction of compound 19 with a carbamyl chloride or isocyanate respectively followed by removal of L. The sulfamyl sulfamide 25 can be prepared by reaction of compound 19 with a sulfamyl chloride (Matier and Conmer *J. Med. Chem.* 1972, 15, 538) under the same conditions. It is noted that these reaction schemes described here can be also used with the advanced intermediates 7b shown in Scheme 8.

SCHEME 12

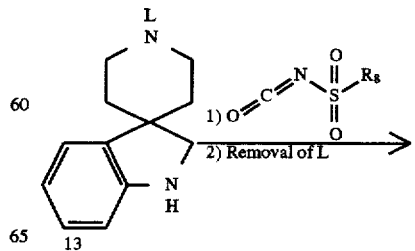

SCHEME 12 -continued

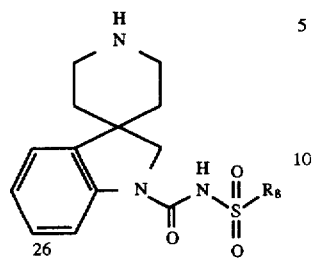

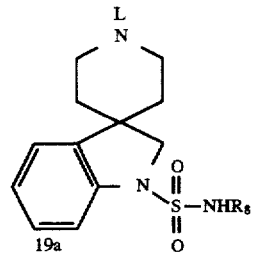

Reaction of compound 13 with sulfonyl isocyanate gives the sulfonyl urea 26 after removal of the protecting group L. It is noted that the reaction can be also used with the advanced intermediates 7a shown in Scheme 7.

SCHEME 13

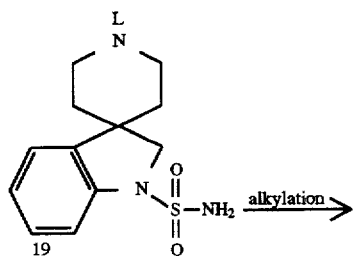

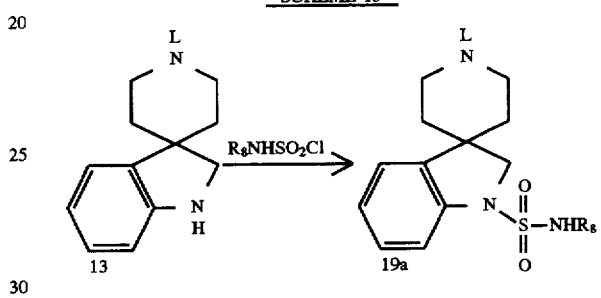

Substituted sulfamide or urea such as compound 19a can be prepared from intermediate 19 by alkylation with an alkyl or aryl alkyl halide or other activated alkyl groups using a base such as sodium hydride in an inert solvent such as THF or DMF. Removal of the protective group L gives the piperidine ready for further reaction. It is noted that this reaction can also be carried out on advanced intermediates such as compound 7b.

SCHEME 14

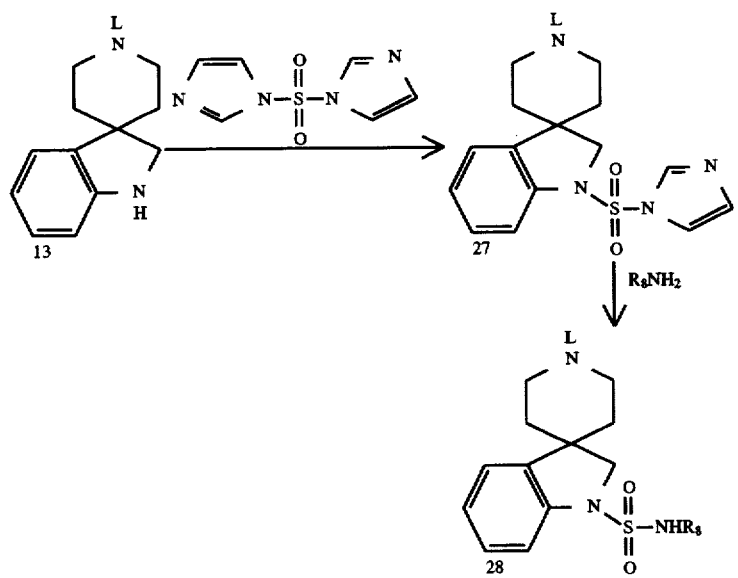

Alternatively, the substituted sulfamide can also be prepared by reaction of the indoline 13 with a substituted sulfamoyl chloride, which is either commercially available or can be conveniently prepared by procedures in the literature (for example J. A. Kloek and K. L. Leschinsky *J. Org. Chem.*, Vol. 41, No. 25, 1976, 4028–4029; W. L. Matier & W. T. Comer *J. Med. Chem.* 1972, vol 15, No.5 538–541), while the substituted ureas can be prepared by reaction of compound 13 with isocyanate. Removal of the protective group L gives the piperidine which may be employed in further reactions.

The sulfamide or the urea can also be prepared by reaction of compound 13 with 1,1'-sulfonyldiimidazole or 1,1'-carbonyldiimidazole followed by reaction with amines $R_8NH_2$ to yield sulfamide of structure 28 or the urea analog. Removal of the protective group L gives the piperidine ready for further reaction. It is noted that these reactions can also be carried out on advanced intermediates such as 7a.

It is noted that the order of carrying out the foregoing reaction schemes may be varied to facilitate the reaction or to avoid unwanted reaction products.

The utility of the compounds of the present invention as growth hormone secretagogues may be demonstrated by methodology known in the art, such as an assay described by Smith, et al., *Science*, 260, 1640–1643 (1993) (see text of FIG. 2 therein). In particular, the intrinsic growth horomone secretagogue activities of the compounds of the present invention may be demonstrated by this assay. The compounds of the following examples have activity in the aforementioned assay in the range of 0.1 nm to 5 µm.

The growth hormone releasing compounds of Formula I are useful in vitro as unique tools for understanding how growth hormone secretion is regulated at the pituitary level. This includes use in the evaluation of many factors thought or known to influence growth hormone secretion such as age, sex, nutritional factors, glucose, amino acids, fatty acids, as well as fasting and non-fasting states. In addition, the compounds of this invention can be used in the evaluation of how other hormones modify growth hormone releasing activity. For example, it has already been established that somatostatin inhibits growth hormone release and that the growth hormone releasing factor (GRF) stimulates its release. Other hormones that are important and in need of study as to their effect on growth hormone release include the gonadal hormones, e.g., testosterone, estradiol, and progesterone; the adrenal hormones, e.g., cortisol and other corticoids, epinephrine and norepinephrine; the pancreatic and gastrointestinal hormones, e.g., insulin, glucagon, gastrin, secretin; the vasoactive peptides, e.g., bombesin, the neurokinins; and the thyroid hormones, e.g., thyroxine and triiodothyronine. The compounds of Formula I can also be employed to investigate the possible negative or positive feedback effects of some of the pituitary hormones, e.g., growth hormone and endorphin peptides, on the pituitary to modify growth hormone release. Of particular scientific importance is the use of these compounds to elucidate the subcellular mechanisms mediating the release of growth hormone.

The compounds of Formula I can be administered to animals, including man, to release growth hormone in vivo. For example, the compounds can be administered to commercially important animals such as swine, cattle, sheep and the like to accelerate and increase their rate and extent of growth, to improve feed efficiency and to increase milk production in such animals. In addition, these compounds can be administered to humans in vivo as a diagnostic tool to directly determine whether the pituitary is capable of releasing growth hormone. For example, the compounds of Formula I can be administered in vivo to children. Serum samples taken before and after such administration can be assayed for growth hormone. Comparison of the amounts of growth hormone in each of these samples would be a means for directly determining the ability of the patient's pituitary to release growth hormone.

Accordingly, the present invention includes within its scope pharmaceutical compositions comprising, as an active ingredient, at least one of the compounds of Formula I in association with a pharmaceutical carrier or diluent. Optionally, the active ingredient of the pharmaceutical compositions can comprise an anabolic agent in addition to at least one of the compounds of Formula I or another composition which exhibits a different activity, e.g., an antibiotic growth permittant or an agent to treat osteoporosis or in combination with a corticosteroid to minimize the catabolic side effects or with other pharmaceutically active materials wherein the combination enhances efficacy and minimizes side effects.

Growth promoting and anabolic agents include, but are not limited to, TRH, diethylstilbesterol, estrogens, β-agonists, theophylline, anabolic steroids, enkephalins, E series prostaglandins, retinoic acid, compounds disclosed in U.S. Pat. No. 3,239,345, e.g., zeranol, and compounds disclosed in U.S. Pat. No. 4,036,979, e.g., sulbenox, or peptides disclosed in U.S. Pat. No. 4,411,890.

A still further use of the compounds of this invention is in combination with other growth hormone secretagogues such as the growth hormone releasing peptides GHRP-6, GHRP-1 as described in U.S. Pat. Nos. 4,411,890 and publications WO 89/07110, WO 89/07111 and B-HT920 as well as hexarelin and GHRP-2 as described in WO 93/04081 or growth hormone releasing hormone (GHRH, also designated GRF) and its analogs or growth hormone and its analogs or somatomedins including IGF-1 and IGF-2 or α-adrenergic agonists such as clonidine or serotonin 5HTID agonists such as sumitriptan or agents which inhibit somatostatin or its release such as physostigmine and pyridostigmine. In particular, the compounds of this invention may be used in combination with growth hormone releasing factor, an analog of growth hormone releasing factor, IGF-1, or IGF-2. For example, a compound of the present invention may be used in combination with IGF-1 for the treatment or prevention of obesity. In addition, a compound of this invention may be employed in conjunction with retinoic acid to improve the condition of musculature and skin that results from intrinsic aging.

The present invention is further directed to a method for the manufacture of a medicament for stimulating the release of growth hormone in humans and animals comprising combining one of the compounds of the present invention with a pharmaceutical carrier or diluent.

As is well known to those skilled in the art, the known and potential uses of growth hormone are varied and multitudinous. Thus, the administration of the compounds of this invention for purposes of stimulating the release of endogenous growth hormone can have the same effects or uses as growth hormone itself. These varied uses may be summarized as follows: treating growth hormone deficient adults; prevention of catabolic side effects of glucocorticoids; treatment of osteoporosis; stimulation of the immune system, acceleration of wound healing; accelerating bone fracture repair; treatment of growth retardation; treating acute or chronic renal failure or insufficiency; treatment of physiological short stature, including growth hormone deficient children; treating short stature associated with chronic illness; treating obesity and growth retardation associated with obesity; treating growth retardation associated with Prader- Willi syndrome and Turner's syndrome; accelerating the recovery and reducing hospitalization of burn patients or following major surgery such as gastrointestinal surgery; treatment of intrauterine growth retardation, and skeletal dysplasia, treatment of peripheral neuropathies; replacement of growth hormone in stressed patients; treatment of osteochondrody-splasias, Noonans syndrome, schizophrenia, depression, Alzheimer's disease, delayed wound healing, and psychosocial deprivation; treatment of pulmonary dysfunction and ventilator dependency; attenuation of protein catabolic response after a major operation; treating malabsorption syndromes; reducing cachexia and protein loss due to chronic illness such as cancer or AIDS; accelerating weight gain and protein accretion in patients on TPN (total parenteral nutrition); treatment of hyperinsulinemia including nesidioblastosis; adjuvant treatment for ovulation induction and to prevent and treat gastric and duodenal ulcers; stimulation of thymic development and prevention of the age-related decline of thymic function; adjunctive therapy for patients on chronic hemodialysis; treatment of immunosuppressed patients and to enhance antibody response following vaccination; increasing the total lymphocyte count of a human, in particular, increasing the $T_4/T_8$-cell ratio in a human with a depressed $T_4/T_8$-cell ratio resulting, for example, from infection, such as bacterial or viral infection, especially infection with the human immunodeficiency virus; treatment of syndromes manifested by non-restorative sleep and musculoskeletal pain, including fibromyalgia syndrome or chronic fatigue syndrome; improvement in muscle strength, mobility, maintenance of skin thickness, metabolic homeostasis, renal hemeostasis in the frail elderly; stimulation of osteoblasts, bone remodelling, and cartilage growth; stimulation of the immune system in companion animals and treatment of disorders of aging in companion animals; growth promotant in livestock; and stimulation of wool growth in sheep. Further, the instant compounds are useful for increasing feed efficiency, promoting growth, increasing milk production and improving the carcass quality of livestock. Likewise, the instant compounds are useful in a method of treatment of diseases or conditions which are benefited by the anabolic effects of enhanced growth hormone levels that comprises the administration of an instant compound.

In particular, the instant compounds are useful in the prevention or treatment of a condition selected from the group consisting of: osteoporosis; catabolic illness; immune deficiency, including that in individuals with a depressed $T_4/T_8$ cell ratio; hip fracture; musculoskeletal impairment in the elderly; growth hormone deficiency in adults or in children; obesity; cachexia and protein loss due to chronic illness such as AIDS or cancer; and treating patients recovering from major surgery, wounds or burns, in a patient in need thereof.

In addition, the instant compounds may be useful in the treatment of illnesses induced or facilitated by corticotropin releasing factor or stress- and anxiety-related disorders, including stress-induced depression and headache, abdominal bowel syndrome, immune suppression, HIV infections, Alzheimer's disease, gastrointestinal disease, anorexia nervosa, hemorrhagic stress, drug and alcohol withdrawal symptoms, drug addiction, and fertility problems.

It will be known to those skilled in the art that there are numerous compounds now being used in an effort to treat the diseases or therapeutic indications enumerated above. Combinations of these therapeutic agents some of which have also been mentioned above with the growth hormone secretagogues of this invention will bring additional, complementary, and often synergistic properties to enhance the growth promotant, anabolic and desirable properties of these various therapeutic agents. In these combinations, the therapeutic agents and the growth hormone secretagogues of this invention may be independently present in dose ranges from one one-hundredth to one times the dose levels which are effective when these compounds and secretagogues are used singly.

Combined therapy to inhibit bone resorption, prevent osteoporosis and enhance the healing of bone fractures can be illustrated by combinations of bisphosphonates and the growth hormone secretagogues of this invention. The use of bisphosphonates for these utilities has been reviewed, for example, by Hamdy, N. A. T., "Role of Bisphosphonates in Metabolic Bone Diseases" *Trends in Endocrinol. Metab.*, 4, 19–25 (1993). Bisphosphonates with these utilities include alendronate, tiludronate, dimethyl-APD, risedronate, etidronate, YM-175, clodronate, pamidronate, and BM-210995. According to their potency, oral daily dosage levels of the bisphosphonate of between 0.1 mg and 5 g and daily dosage levels of the growth hormone secretagogues of this invention of between 0.01 mg/kg to 20 mg/kg of body weight are administered to patients to obtain effective treatment of osteoporosis.

In the case of alendronate daily oral dosage levels of 0.1 mg to 50 mg are combined for effective osteoporosis therapy with 0.01 mg/kg to 20 mg/kg of the growth hormone secretagogues of this invention.

Osteoporosis and other bone disorders may also be treated with compounds of this invention in combination with calcitonin, estrogens, raloxifene and calcium supplements such as calcium citrate.

Anabolic effects especially in the treatment of geriatric male patients are obtained with compounds of this invention in combination with anabolic steroids such as oxymetholone, methyltesterone, fluoxymesterone and stanozolol.

The compounds of this invention can be administered by oral, parenteral (e.g., intramuscular, intraperitoneal, intravenous or subcutaneous injection, or implant), nasal, vaginal, rectal, sublingual, or topical routes of administration and can be formulated in dosage forms appropriate for each route of administration.

Solid dosage forms for oral administration include capsules, tablets, pills, powders and granules. In such solid dosage forms, the active compound is admixed with at least one inert pharmaceutically acceptable carrier such as sucrose, lactose, or starch. Such dosage forms can also comprise, as is normal practice, additional substances other than inert diluents, e.g., lubricating agents such as magnesium stearate. In the case of capsules, tablets and pills, the dosage forms may also comprise buffering agents. Tablets and pills can additionally be prepared with enteric coatings.

Liquid dosage forms for oral administration include pharmaceutically acceptable emulsions, solutions, suspensions, syrups, the elixirs containing inert diluents commonly used in the art, such as water. Besides such inert diluents, compositions can also include adjuvants, such as wetting agents, emulsifying and suspending agents, and sweetening, flavoring, and perfuming agents.

Preparations according to this invention for parenteral administration include sterile aqueous or non-aqueous solutions, suspensions, or emulsions. Examples of non-aqueous solvents or vehicles are propylene glycol, polyethylene glycol, vegetable oils, such as olive oil and corn oil, gelatin, and injectable organic esters such as ethyl oleate. Such dosage forms may also contain adjuvants such as preserving, wetting, emulsifying, and dispersing agents. They may be sterilized by, for example, filtration through a bacteria-retaining filter, by incorporating sterilizing agents into the compositions, by irradiating the compositions, or by heating the compositions. They can also be manufactured in the form of sterile solid compositions which can be dissolved in sterile water, or some other sterile injectable medium immediately before use.

Compositions for rectal or vaginal administration are preferably suppositories which may contain, in addition to the active substance, excipients such as cocoa butter or a suppository wax.

Compositions for nasal or sublingual administration are also prepared with standard excipients well known in the art.

The dosage of active ingredient in the compositions of this invention may be varied; however, it is necessary that the amount of the active ingredient be such that a suitable dosage form is obtained. The selected dosage depends upon the desired therapeutic effect, on the route of administration, and on the duration of the treatment. Generally, dosage levels of between 0.0001 to 10 mg/kg. of body weight daily are administered to patients and animals, e.g., mammals, to obtain effective release of growth hormone.

The following examples are provided for the purpose of further illustration only and are not intended to be limitations on the disclosed invention.

INTERMEDIATE 1

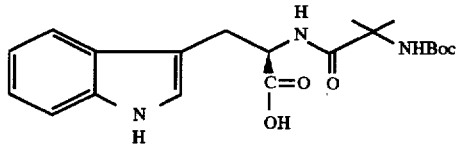

Step A

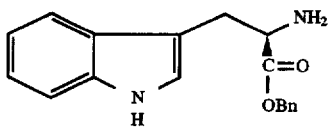

To a solution of the commercially available N-t-BOC-D-tryptophan (25.0 g, 82.2 mmol), benzyl alcohol (10.2 mL, 98.6 mmol), and DMAP (100 mg) in dichloromethane (200 mL) at 0° C., was added EDC (17.4 g, 90.4 mmol) in several portions over one hour period. The reaction mixture was stirred at room temperature for six hours and was poured into water (200 mL), and the organic layer was separated. The organic solution was washed with a mixture of brine and 3N hydrochloric acid dried over anhydrous magnesium sulfate, filtered and concentrated to give a thick oil, which solidified upon standing.

To a solution of this oil in 30 mL of dichloromethane was added 20 mL of TFA and stirred for 1 h. The reaction mixture was concentrated, neutralized carefully with saturated aqueous sodium bicarbonate solution, and extracted with dichloromethane (2×100 mL). The combined organic solution were washed with brine (100 mL), passed through a short column of silica gel eluting with 5–10% methanol in dichloromethane to give 23.2 g of the amine as an oil after evaporation.

Step B

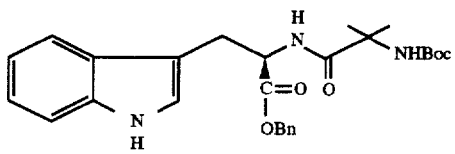

To a solution of the above product, HOBT (10.6 g, 78.8 mmol), N-BOC-α-methyl alanine (19 g, 94.5 mmol) in 200 mL of dichloromethane, was added EDC (19.5 g, 0.102 mol) in several portions at 0° C. After 5 minutes, the clear reaction mixture became milky. After stirring at room temperature overnight, the reaction mixture was poured into 200 mL of water and the organic layer was separated. The organic solution was washed with brine, brine and saturated sodium bicarbonate solution, dried over anhydrous magnesium sulfate, filtered and concentrated to give a thick oil, which was purified by flash chromatography eluting with 10–40% ethyl acetate in hexane to give the desired material (28.7 g).

$^1$H NMR (CDCl$_3$, 200 MHz) δ8.48 (br.s, 1H), 7.54 (br.d, 1H), 7.38–7.23 (m, 3H), 7.19 (br.d, 2H), 7.15–7.00 (m, 1H), 6.90 (d, 1H), 6.86 (d, 1H), 5.06 (br.s, 2H), 4.95 (ddd, 1H), 3.30 (2dd, 2H), 1.40 (s, 15H)

Step C

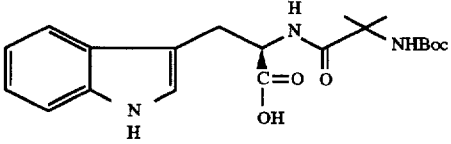

A solution of the material from Step A (28.7 g) in 200 mL of ethanol was stirred at RT under a H$_2$ balloon for 20 minutes in the presence of 10% palladium on carbon. (2 g). The catalyst was filtered off through a pad of celite and washed with ethyl acetate. The filtrate was concentrated to give the acid as a slightly pink foam (23.3 g).

$^1$H NMR (CDCl$_3$, 200 MHz) δ8.60 (br.s, 1H), 7.55 (d, 1H), 7.26–6.90 (m, 3H), 6.88 (br.d, 1H), 4.80 (m, 1H), 3.32 (2 dd, 2H), 1.37 (s, 3H), 1.35 (s, 12H).

INTERMEDIATE 2

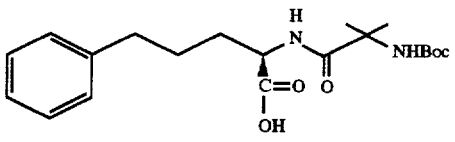

Step A
(DL)-N-acetyl-2-amino-5-phenylpentanoic acid

To a solution of sodium (2.3 g, 0.1 mol) in ethanol (60 mL) under nitrogen at room temperature, was added diethyl acetamidomalonate. The mixture was stirred at room temperature for one hour, and then 1-bromo-3-phenylpropane was added dropwisely. After the addition, the mixture was stirred at room temperature for two hours, then refluxed overnight. It was cooled to room temperature and partitioned between water and ethyl acetate. The organic layer was washed with sodium bicarbonate in water and dried over MgSO$_4$ and evaporated to give an intermediate (32.5 g, 97%).

$^1$H NMR (CDCl$_3$, 400MHz) 7.26–7.10 (m, 5H); 6.75 (br. s, 1H); 4.19 (q, J=7 Hz, 4H); 2.58 (t, J=7.9 Hz, 2H); 2.39–2.35 (m, 2H); 2.00 (s, 3 H); 1.43–1.39 (m, 2H); 1.20 (t, J=7 Hz, 6H).

The product above was suspended in 190 mL of 2.5N NaOH in water and refluxed for two hours. The mixture was cooled to 0° C., and it was carefully neutralized 6N HCl to pH=2. The precipitate was collected through a glass sinter funnel and washed with small amount of cold water and air dried. The solid was then suspended in 300 mL of water and refluxed for four hours. The solution was cooled and acidified to pH=1 and the solid was collected by filtration (15.3 g, 67%).

$^1$H NMR (CD3OD, 400 MHz) 7.26–7.12 (m, 5H); 4.90,4.37 (m, 1H); 2.65–2.60 (m, 2H); 1.97 (s, 3H); 1.87 –1.82 (m, 1H); 1.73–1.65 (m, 3H).

Step B (D)-N-acetyl-2-amino-5-phenylpentanoic acid

The racemic intermediate from last step (10 g, 42.5 mmol) and CoCl3-6H2O was dissolved in 21 ml of 2N KOH and 200 mL of water at 40° C., and the pH of the solution was adjusted to 8 by addition of the several drops of 2N KOH. The acylase I (Aspergillus sp, 0.5 u/mg, from Sigma; 0.9 g) was added with vigorous stirring. The reaction mixture was stirred for one day at 40° C. and the pH was kept at 8 by addition of a few drops of KOH. The solid formed was filtered. The filtrate was acidified by 3N HCl to pH=2, and was extracted by ethyl acetate (200 mL×4). The organic extracts were combined and evaporated to give a white solid (4.64 g, 46%)

$^1$H NMR (CD3OD, 400MHz) 7.26–7.12 (m, 5H); 4.90–4.37 (m, 1H); 2.65–2.60 (m, 2H); 1.97 (s, 3H); 1.87–1.82 (m, 1H); 1.73–1.65 (m, 3H).

Step C (D)-N-t-Boc-2-amino-5-phenylpentanoic acid

The intermediate from step B (4.2 g, 17.8 mmol) was suspended in 2N HCl (100 mL) and refluxed for two hours. The reaction mixture was evaporated in vacuo to remove water and hydrochloric acid to yield a white solid.

To a solution of the solid in 50 mL of water, was added 3 N NaOH until the pH=11, then di-t-butyl dicarbonate (4.66 g, 21.4 mmol) was added with vigorous stirring. After four hours, the reaction mixture was acidified to pH=2 with 3N HCl and it was extracted with ethyl acetate (100 mL×3). The organic extract were combined and evaporated to give a white solid (6.56 g, crude) which was used without purification.

$^1$H NMR (CD3OD, 400 MHz) 7.26–7.12 (m, 5H); 4.11–4.08 (m, 1H); 2.65–2.60 (m, 2H); 1.83–1.62 (m, 4H); 1.43 (s, 9H).

Step D

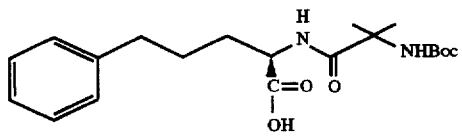

Following the procedures from the preparation of Intermediate 1 using (D)-N-t-Boc-2-amino-5-phenylpentanoic acid in the place of N-t-BOC-D-tryptophan gave Intermediate 2.

$^1$H NMR (CDCl$_3$, 400 MHz) 7.24–7.20 (m, 2H), 7.15–7.04 (m, 3H), 4.60–4.55 (m, 1H), 2.62–2.55 (m, 2H), 2.00–1.86 (m, 1H), 1.78–1.60 (m, 3H), 1.50 (s, 6H), 1.30 (s, 9H).

EXAMPLE 1

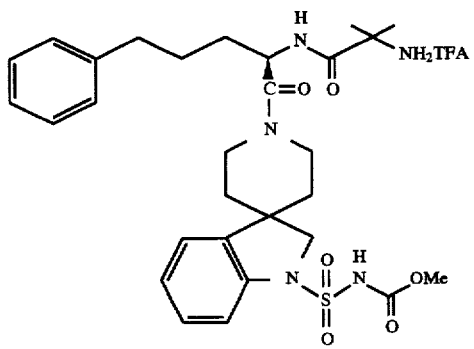

Step A

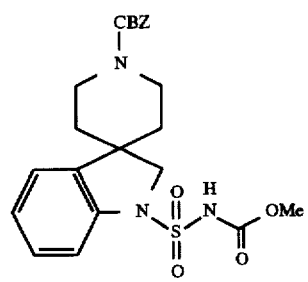

To a round bottom flask equipped with a magnetic bar were added to the CBZ protected spiroindoline 13 (H. Ong et al *J. Med. Chem.* 1983, 23, 981–986) (12.9 g, 40.0 mmol), diisopropyl ethyl amine (5.17 g, 40.0 mmol) and methylene chloride (120 ml). Once the starting material was dissolved, the mixture was cooled to 0° C. and then of methyl (chlorosulfonyl) carbamate (8.33 g) was added slowly. Stirring was kept at 0° C. for 30 minutes, and then at room temperature for another 30 minutes. The reaction mixture was diluted with 150 ml methylene chloride and washed with brine, and then the aqueous layer was further extracted with methylene chloride (X1). The organic layers were combined, dried over sodium sulfate and concentrated in vacuo. Flash chromatography (silica gel; hexane-ethyl acetate as eluent) provided the desired product as white solid (15.3 g).

$^1$HNMR (CDCl$_3$, 400 MHz) d 7.70 (br.s, 1H), 7.70–7.06 (m, 4H), 5.15 (s, 2H), 4.24 (s, 2H), 3.66 (s, 3H), 2.93 (br.s, 2H), 1.82–1.70 (m, 4H). FAB-MS calc. for C$_{22}$H$_{25}$N$_3$O$_6$S: 459; Found: 460 (M+1).

Step B

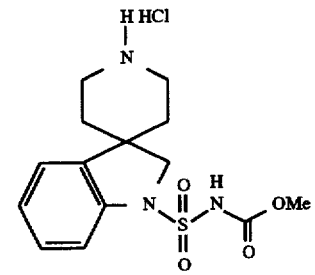

To a solution of the compound obtained (13.0 g, 28.3 mmol) from Step 1 in methanol-ethyl acetate solution (300 ml, 5:1) were added concentrated hydrochloride (2.36 ml, 28.3 mmol) and 20% Pd(OH)$_2$/C (2.6 g). Under a hydrogen balloon, the reaction mixture was stirred at room temperature for 4 hours. The catalyst was removed by filtration and the filtrate was concentrated in vacuo to give the desired product as white solid (7.58 g).

¹HNMR (CDCl₃, 400 MHz) δ7.27–7.25 (m, 3H), 7.11–7.07 (m, 1H), 4.31 (s, 2H), 3.61 (s, 3H), 3.48 (br.s, 1H), 3.44 (br.s, 1H), 3.20 (t, 1H), 3.19 (t, 1H), 2.13 (t, 1H), 2.12 (t, 1H), 1.98 (s, 1H), 1.95 (s, 1H). FAB-MS calc. for C₁₄H₁₉N₃O₄S: 325; Found: 326 (M+1).

Step C

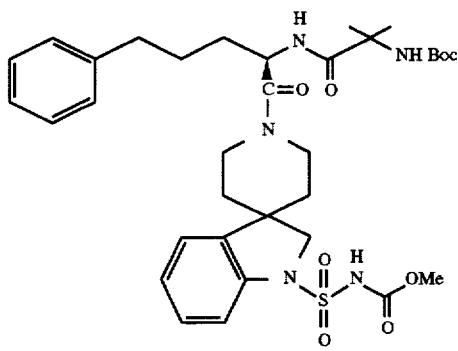

To a solution of the compound obtained from step 2 (250.0 mg, 0.69 mmol), Intermediate 2 (261.0 mg, 0.69 mmol), NMM (140.0 ml, 1.38 mmol) and HOBT (93.0 mg, 0.69 mmol) in methylene chloride (10 ml) was slowly added EDC (198.0 mg, 1.04 mmol). The reaction mixture was allowed to stir at room temperature overnight. The reaction was diluted with methylene chloride and washed with 2N HCl aqueous solution. The organic layer was separated, dried over sodium sulfate and concentrated in vacuo to give the crude product, which was brought to flash column chromatography (silica gel, hexane-ethyl acetate-acetic acid as eluent) to give the desired product as white solid (137.7 mg).

FAB-MS calc. for C₃₄H₄₇N₅O₈: 685 found: 686 (M+1).

Step D

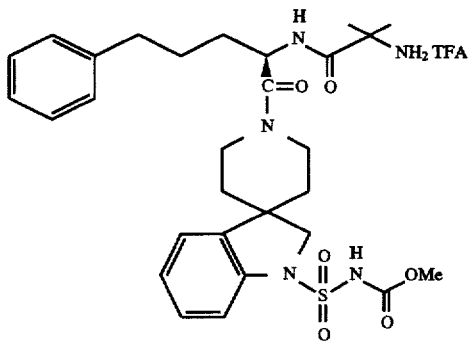

The compound (250.0 mg) obtained from step 3 was dissolved in 2 ml methylene chloride, followed by addition of 8 ml trifluoroacetic acid. The reaction mixture was allowed to stir at room temperature for 4 hours, and then 10 ml toluene was added to the reaction flask. The reaction mixture was concentrated in vacuo to provide 235.0 mg of the desired product.

¹HNMR (CDCl₃, 400 MHz) δ7.29–7.01 (m, 9H); 4.52–4.44 (br.m, 1H); 4.26 (dd 2H); 3.95–3.82 (m); 3.63 (s, 3H); 3.30–3.18 (br. dd), 2.88–2.75 (m); 2.75–2.60 (m); 2.02–1.94 (dt, 1H); 1.80–1.65 (m), 1.62 (s); 1.60 (s). FAB-MS calc. for C₂₉H₃₉N₅O₆: 585 found: 586 (M+1).

Additional growth hormone secretagogues shown in Tables I were prepared according to the established procedure shown in Examples 1 using the appropriate alkyl-(chlorosulfonyl)carbamate instead of methyl-(chlorosulfonyl)carbamate, which was prepared from the reaction of an alcohol with chlorosulfonyl isocyanate (Burgess et al, Organic Syntheses vol. VI, 788), to react with the intermediate in example 1 step A. For example, the use of ethanol instead of methanol led to the following compound.

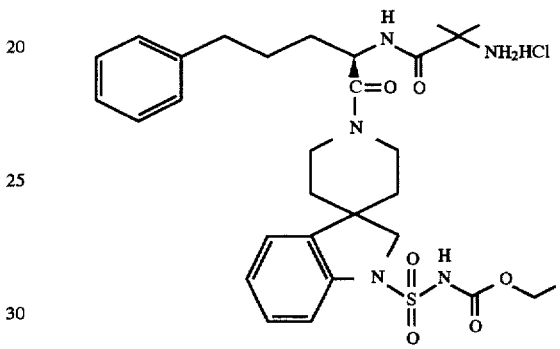

¹HNMR (CDCl₃, 400 MHz) δ7.29–7.01 (m, 9H); 4.50–4.47 (m 1H), 4.25 (appeared as d, 2H); 4.06 (q, J=7.1 Hz, 2H); 3.94–3.85 (br. m, 1H), 3.29–3.20 (m, 2H), 2.89–2.60 (m, 3H), 2.05–1.95 (m, 1H), 1.80–1.65 (m), 1.62 (s), 1.60 (s), 1.14 (t, J=7.1 Hz, 3H).

FAB-MS calc. for C₃₀H₄₁N₅O₆: 599 found: 600 (M+1).

EXAMPLE 2

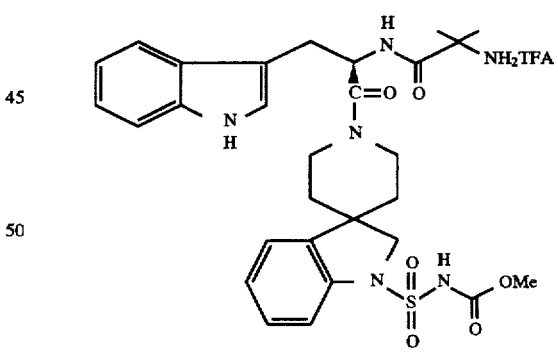

The compound was prepared by the procedure described in Example 1, except that Intermediate 1 was used instead of Intermediate 2. FAB-MS calc. for C₂₉H₃₆N₆O₆S:596 found: 597(M+1).

INTERMEDIATE 3

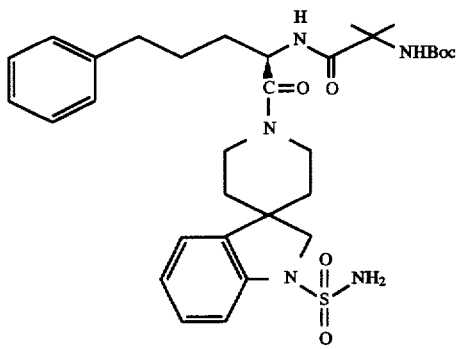

Step A

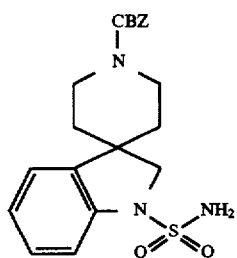

To a round bottom flask charged with of chlorosulfonyl isocyanate (13.3 g, 93.6 mmol), was added formic acid (4.2 g, 93.6 mmol) dropwise while the temperature was kept below 5° C. The reaction mixture was allowed to stir at room temperature until gas evolution ceased. To this resulting sulfamoyl chloride mixture was slowly added a solution of the spiroindoline (23.4 g, 72 mmol) and diisopropylethyl amine (10.2 g, 79.2 mmol) in THF (250 ml). The reaction mixture was allowed to stir at room temperature overnight, and then was poured to cold 2N HCl solution and extracted with methylene chloride three times. Organic layers were combined, dried and concentrated to provide a yellow oil, which was brought to flash column chromatography (silica gel, 40% ethyl acetate in hexane) to provide 20.7 g of the desired product as white solid.

¹HNMR (CDCl₃, 400 MHz) d 7.41–7.02 (m, 9H), 5.14 (s, 2H), 4.81 (s, 2H), 4.19 (br.s, 2H), 3.81 (s, 2H), 2.94 (br.s, 2H), 1.83–1.64 (m, 4H). FAB-MS calc. for C₂₀H₂₃N₃O₄S: 401, Found: 402 (M+1).

Step B

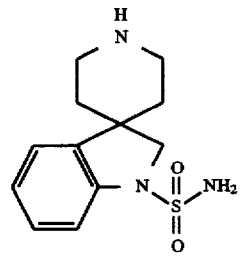

A suspension of 10% palladium on carbon (100 mg) and the intermediate from the previous step (838 mg, 2.1 mmol) in ethanol (20 mL) was stirred under a hydrogen atmosphere overnight at room temperature. The reaction mixture was then filtered through celite and evaporated to give the product (568 mg, 100%).

¹H NMR (CD₃OD, 400 MHz): δ7.37 (d, J=7.8 Hz, 1H); 7.21–7.15 (m, 2H), 7.01 (dt, J=7.2, 1.0 Hz, 1H); 3.83 (s, 2H); 3.06 (br. td, 2H), 2.77 (dt, J=2.8, 13 Hz, 2H); 1.86 (dt, J=4.2, 13.5 Hz, 2H); 1.68 (br.d, J=13.5 Hz, 2H). FAB-MS calc. for C₁₂H₁₇N₃O₂S: 267; Found 268 (M+H).

Step C

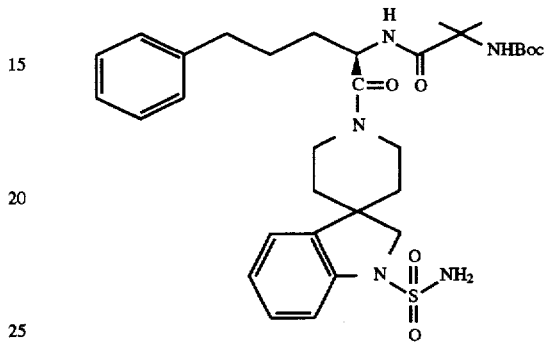

To a solution of the intermediate prepared in the previous step (544 mg, 2.03 mmol), Intermediate 2 (770 mg, 2.03 mmol), and HOBT (275 mg, 2.03 mmol) in dichloromethane at 0° C. was added EDC (1.5 eq.). The reaction mixture was stirred overnight during which time the temperature was warmed to ambient temperature. The solution was washed with 3N hydrochloric acid, saturated sodium bicarbonate and brine, dried over anhydrous magnesium sulfate; then filtered and concentrated. Purification by MPLC eluting with 70% ethyl acetate in hexane gave the product (1.05 g, 82%).

¹H NMR (CD₃OD, 400 MHz): δ7.64 (dd, J=8.5, 11.8 Hz, 1H), 7.38 (d, J=7.5 Hz, 1H); 7.26–6.92 (m, 7H); 4.95–4.82 (m, 1H); 4.46 (br. d, J=13.3 Hz, 1H); 3.90–3.80 (dd, 2H); 3.28–3.12 (m, 1H); 2.88–2.80 (m, 1H); 2.70–2.64 (m, 2H); 2.00–1.52 (m); 1.42 (s); 1.38 (s)

FAB-MS calc. for C₃₂H₄₅N₅O₆S: 627 found: 628 (M+1).

EXAMPLE 3

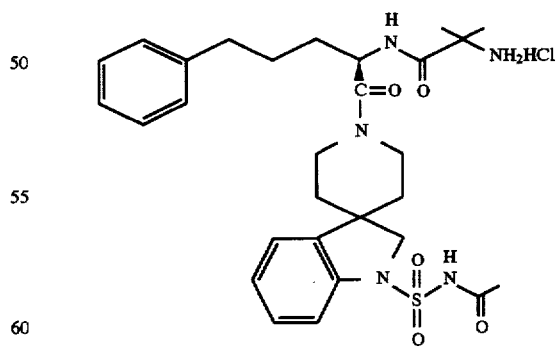

Step A

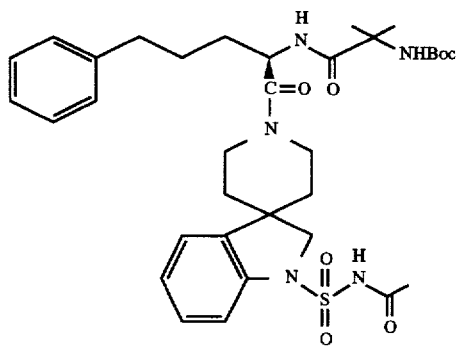

To a stirred solution of the intermediate from previous step (250 mg, 0.398 mmol), NMM (0.13 mL, 1.2 mmol), and DMAP (10 mg) in dichloromethane (10 mL) at 0° C. was added acetic anhydride (0.075 mL, 0.8 mmol). The reaction mixture was stirred at 0° C. for 1 h, and TLC (silica gel, developing with 80% ethyl acetate in hexane) indicated the reaction was over. The reaction mixture was diluted with ethyl acetate (20 mL) and washed with 3N hydrochloric acid and brine; dried over anhydrous magnesium sulfate; then filtered and concentrated. Purification by MPLC eluting with 80% ethyl acetate in hexane gave the product (216 mg, 82%).

$^1$HNMR (CDCl$_3$, 400 MHz) δ7.29–7.01 (m, 9H); 4.52–4.44 (br. m, 1H); 4.26 (dd 2H); 3.95–3.82 (m); 3.63 (s, 3H); 3.30–3.18 (br. dd), 2.88–2.75 (m); 2.75–2.60 (m); 2.02–1.94 (dt, 1H); 1.80–1.65 (m), 1.62 (s); 1.60 (s). FAB-MS calc. for C$_{34}$H$_{47}$N$_5$O$_7$S: 669 found: 670 (M+1)

Step B

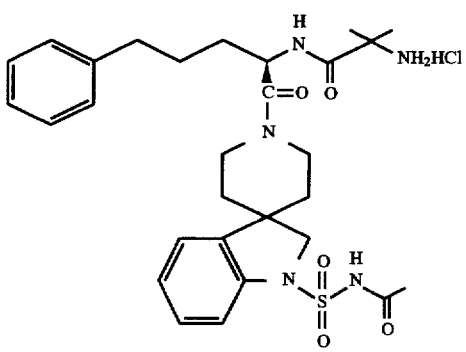

A solution of the compound from Step A (196 mg) in ethyl acetate (5 mL) was cooled to 0° C. While stirring, hydrogen chloride gas was bubbled into the mixture until saturation occurred. The reaction was stirred for 15 minutes. The solution was then concentrated to remove ethyl acetate. The residue was then redissolved in dichloromethane and hexane followed by evaporation in vacuo to afford the product as a solid (170 mg).

FAB-MS calc. for C$_{29}$H$_{39}$N$_5$O$_5$S: 428; Found: 429 (M+H).

$^1$HNMR (CD$_3$OD, 400 MHz) δ7.28–7.01 (m, 9H); 4.50–4.46 (br. m, 1H); 4.27 (appears as d, 2H); 3.94–3.84 (br. dd, 1H); 3.28–3.16 (b m 1H); 2.86–2.75 (m, 1H); 2.70–2.60 (m, 2H); 1.92 (s, 3H); 1.80–1.50 (m); 1.61 (s). FAB-MS calc. for C$_{29}$H$_{39}$N$_5$O$_6$S: 585 found: 586 (M+1).

EXAMPLE 4

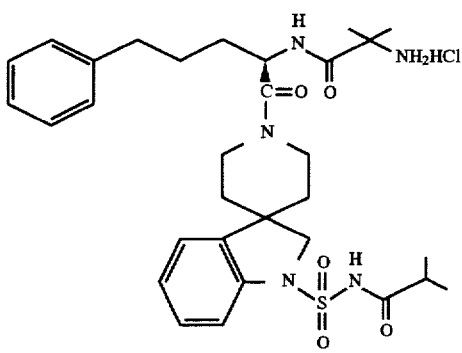

Step A

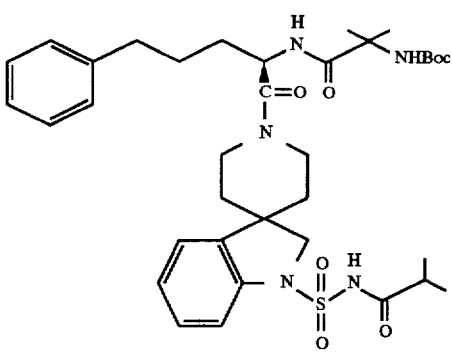

To a stirred solution of the intermediate from step (250 mg, 0.398 mmol), NMM (0.13 mL, 1.2 mmol), and DMAP (10 mg) in dichloromethane (10 mL) at 0° C. was added isobutyryl chloride (0.063 mL, 0.6 mmol). The reaction mixture was stirred at 0° C. for 1 h, and TLC (silica gel, developing with 80% ethyl acetate in hexane) indicated the reaction was over. The reaction mixture was diluted with ethyl acetate (20 mL) and washed with 3N hydrochloric acid and brine; dried over anhydrous magnesium sulfate; then filtered and concentrated. Purification by MPLC eluting with 60% ethyl acetate in hexane gave the product (261.9 mg, 94%).

FAB-MS calc. for C$_{36}$H$_{51}$N$_5$O$_7$S: 697 found: 698 (M+1).

Step B

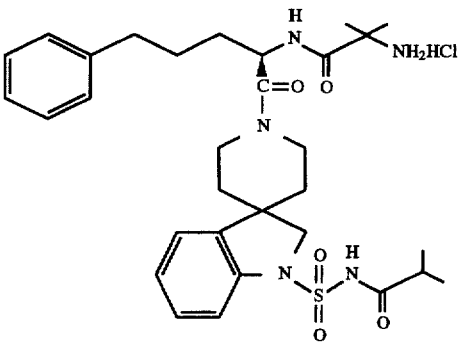

Prepared by the procedure described in Example 1, Step B from the intermediate from the previous step (241 mg, 0.34 mmol) and HCl gas at 0° C. in ethyl acetate (3 mL) for 20 minutes. Product: 200 mg.

$^1$HNMR (CD$_3$OD, 400 MHz) δ7.29–7.01 (m, 9H); 4.52–4.46 (br. m, 1H); 4.30 (apparent d, 2H); 3.95–3.84 (m 1H); 3.32–3.18 (br, dd, 1H); 2.86–2.75 (m, 1H); 2.70–2.60 (m, 2H); 2.42–2.35 (m, 1H); 1.80–1.50 (m); 1.61 (s);.0.93 (d, 6H). FAB-MS calc. for $C_{31}H_{43}N_5O_5S$ 597; Found: 598 (M+H)

The additional growth hormone secretagogues shown in Tables I were prepared according to the established procedure shown in Examples 3 and 4 using the appropriate anhydride or acyl chloride instead of acetic anhydride or isobutyryl chloride to react with the Intermediate 3. The characterization included FAB-MS and NMR studies. Similarly, other analogs can be prepared the same way.

TABLE I

| Example | Acyl chloride | R | molecular formula FAB-MS (M + 1) |
|---|---|---|---|
| 5 | (CH₃)₂CHC(O)Cl (pivaloyl chloride) | t-Bu ketone | $C_{32}H_{45}N_5O_5S$ 612 |
| 6 | benzoyl chloride | phenyl ketone | $C_{34}H_{41}N_5O_5S$ 632 |
| 7 | 4-chlorobenzoyl chloride | 4-Cl-phenyl ketone | $C_{34}H_{40}N_5O_5SCl$ 666 |
| 8 | 4-methoxybenzoyl chloride | 4-OMe-phenyl ketone | $C_{35}H_{43}N_5O_6S$ 662 |
| 9 | diphenylacetyl chloride | diphenylacetyl ketone | $C_{41}H_{47}N_5O_5S$ 722 |
| 10 | phenylacetyl chloride | phenylacetyl ketone | $C_{35}H_{43}N_5O_5S$ 646 |

EXAMPLE 11

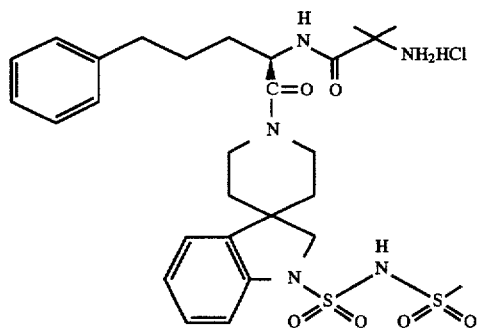

Step A

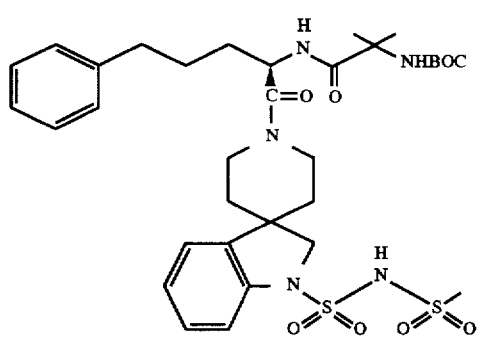

To a stirred solution of the Intermediate 3 (125.6 mg, 0.20 mmol), DMAP (12.2 mg, 0.10 mmol) and diisopropylethylamine (69.0 ml, 0.4 mmol) in methylene chloride (2 ml) was added methanesulfonyl chloride (45.8 mg, 0.4 mmol), and then the reaction mixture was kept stirring at room temperature overnight. The reaction mixture was diluted with methylene chloride and washed with 2N HCl solution once. The organic layer was dried, concentrated and purified silica gel column (1% HOAc:10% MeOH in EtOAc as eluent) to give 66.8 mg of the desired product.

FAB-MS calc. for $C_{33}H_{47}N_5O_8S_2$: 705. Found: 706 (M+1).

Step B

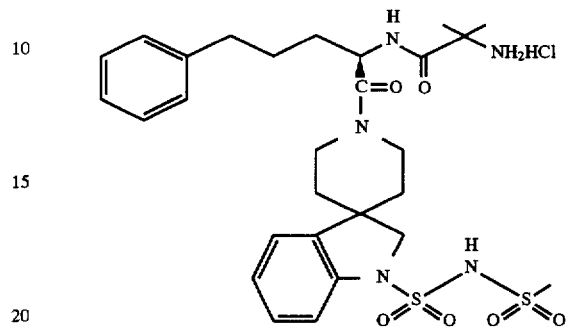

The compound obtained from step 4 was dissolved in ethyl acetate and hydrogen chloride gas was bubble into the mixture until saturation occurred. The reaction solution was allowed to stir at room temperature for 30 minutes, and then small amounts of hexane and methylene were added. This mixture was brought to vacuo to give the desired product as a solid.

FAB-MS calc. for $C_{28}H_{39}N_5O_6S_2$: 605. Found: 606.

The additional growth hormone secretagogues shown in Table II were prepared according to the established procedure shown in Example 5 using the appropriate sulfonyl chloride instead of methanesulfonyl chloride to react with the Intermediate 3. The characterization included FAB-MS and NMR studies. Similarly, other analogs can be prepared the same way.

TABLE II

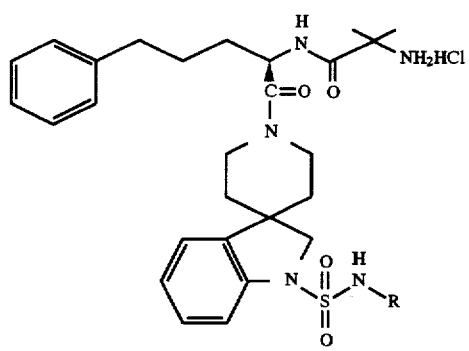

| Example | sulfonyl chloride | R | molecular formula FAB-MS (M + 1) |
|---|---|---|---|
| 12 | (=O)-C6H4-CH3) | (=O)-C6H4-CH3) | $C_{32}H_{42}N_6O_6S$ 639 |

TABLE II-continued

| Example | sulfonyl chloride | R | molecular formula FAB-MS (M + 1) |
|---|---|---|---|
| 13 | (4-methoxyphenyl)sulfonyl chloride | (4-methoxyphenyl)sulfonyl | $C_{32}H_{42}N_6O_7S$ 698 |

EXAMPLE 4

Step A

To a stirred solution of the Intermediate 3 (209 mg, 0.32 mmol), DMAP (12.2 mg, 0.10 mmol) and diisopropylethylamine (83 mg, 0.64 mmol) in methylene chloride (8 ml) was added isobutyl chloroformate (87 mg, 0.64 mmol), and then the reaction mixture was kept stirring at room temperature overnight. The reaction mixture was diluted with methylene chloride and washed with 2N HCl solution once. The organic layer was dried, concentrated and purified on silica gel column (1% HOAc:10% MeOH in EtOAc as eluent) to give 173 mg of the desired product (74%).

FAB-MS calc. for $C_{37}H_{53}N_5O_8S$: 727, Found: 728 (M+1).

Step B

The compound obtained from step 4 was dissolved in ethyl acetate and hydrogen chloride gas was bubble into the mixture until saturation occurred. The reaction solution was allowed to stir at room temperature for 30 minutes, and then small amounts of hexane and methylene were added. This mixture was brought to vacuo to give the desired product as a solid.

FAB-MS calc. for $C_{32}H_{45}N_5O_6S$: 627, Found: 628 (M+1).

The additional growth hormone secretagogues shown in Table III were prepared according to the established procedure shown in Example 14 using the appropriate chloroformate instead of isobutyl chloroformate to react with the Intermediate 3. The characterization included FAB-MS and NMR studies. Similarly, other analogs can be prepared the same way.

TABLE III

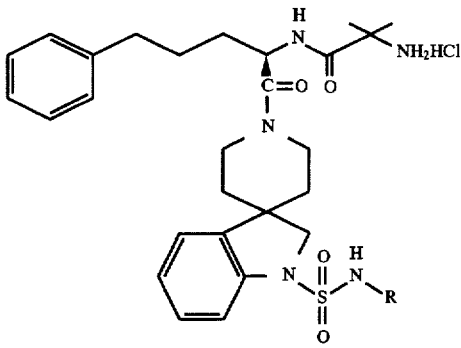

| Example | chloroformate | R | molecular formula FAB-MS (M + 1) |
|---|---|---|---|
| 15 | 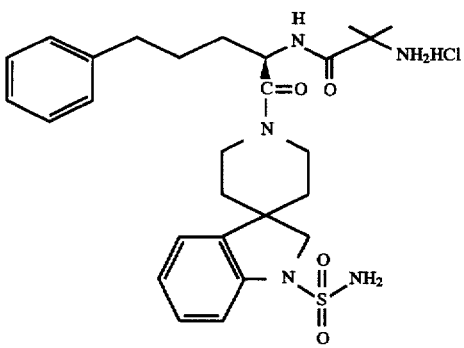 (Cl-C(O)-O-butyl) | (C(O)-O-butyl) | $C_{32}H_{45}N_5O_6S$ 628 |
| 16 | Cl-C(O)-O-CH2-phenyl | C(O)-O-CH2-phenyl | $C_{35}H_{43}N_5O_6S$ 662 |

EXAMPLE 17

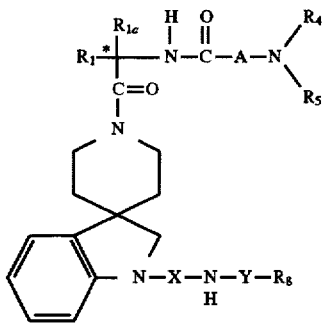

To a stirred solution of the intermediate 3 (200 mg) in ethyl acetate (3 mL) at 0° C., was bubbled HCl gas until it was saturated. The mixture was stirred for 20 minutes, and evaporated to dryness. The solid was washed with small ethyl acetate, dried under vacumm to give the product (174 mg).

$^1$HNMR (DMSO-D6, 400 MHz) δ8.47 (dd, J=8.4, 11.7 Hz, 1H), 8.24 (br. s, 3H); 7.33–6.97 (m, 9H); 4.80–4.76 (br. m, 1H), 4.35 (br. d, J=12.8 Hz, 1H), 3.85 (br. d, 1H), 3.21–3.12 (br. m, 1H), 2.80–2.69 (br. m, 1H), 2.65–2.50 (m, 2H), 1.75–1.55 (m, 8H); 1.49,1.48 (s, 6H) FAB-MS calc. for $C_{27}H_{37}N_5O_4S$: 527, Found: 528 (M+1).

While the invention has been described and illustrated with reference to certain particular embodiments thereof, those skilled in the art will appreciate that various adaptations, changes, modifications, substitutions, deletions, or additions of procedures and protocols may be made without departing from the spirit and scope of the invention. For example, effective dosages other than the particular dosages as set forth herein above may be applicable as a consequence of variations in the responsiveness of the mammal being treated for any of the indications with the compounds of the invention indicated above. Likewise, the specific pharmacological responses observed may vary according to and depending upon the particular active compounds selected or whether there are present pharmaceutical carriers, as well as the type of formulation and mode of administration employed, and such expected variations or differences in the results are contemplated in accordance with the objects and practices of the present invention. It is intended, therefore, that the invention be defined by the scope of the claims which follow and that such claims be interpreted as broadly as is reasonable.

What is claimed is:

1. A compound of the formula I:

wherein:

$R_1$ is selected from the group consisting of: $C_1$-$C_{10}$ alkyl-, aryl-, aryl($C_1$-$C_6$ alkyl)-, heteroaryl-, heteroaryl($C_1$-$C_6$ alkyl)-, ($C_3$-$C_7$ cycloalkyl)-($C_1$-$C_6$ alkyl)-, ($C_1$-$C_5$ alkyl)-K-($C_1$-$C_5$ alkyl)-, aryl-K-($C_1$-$C_5$ alkyl)-, aryl-($C_1$-$C_5$ alkyl)-K-($C_1$-$C_5$ alkyl)-, heteroaryl-K-($C_1$-$C_5$ alkyl)-, heteroaryl-($C_1$-$C_5$ alkyl)-K-($C_1$-$C_5$ alkyl)-, ($C_3$-$C_7$ cycloalkyl)-K-($C_1$-$C_5$ alkyl)-, and ($C_3$-$C_7$ cycloalkyl)-($C_1$-$C_5$ alkyl)-K-($C_1$-$C_5$ alkyl)-, wherein K is —O—, —S(O)$_m$—, —N($R_2$)C(O)—, —C(O)N

47

$(R_2)$—, —OC(O)—, —C(O)O—, —CR$_2$=CR$_2$— or —C≡C—, wherein R$_2$ and the alkyl groups are optionally further substituted with 1 to 9 halo, —S(O)$_m$R$_{2a}$, 1 to 3 of —OR$_{2a}$, or —C(O)OR$_{2a}$, and wherein aryl is phenyl or naphthyl, and heteroaryl is selected from indolyl, thiopheneyl, furanyl, benzothiopheneyl, benzofuranyl, pyridinyl, quinolinyl, triazolyl, imidazolyl, thiazolyl, and benzimidazolyl, wherein aryl and heteroaryl are unsubstituted or substituted with phenyl, phenoxy, halophenyl, 1 to 3 of —C$_1$–C$_6$ alkyl, 1 to 3 of halo, 1 to 2 of —OR$_2$, methylenedioxy, —S(O)$_m$R$_2$, 1 to 2 of —CF$_3$, —OCF$_3$, nitro, —N(R$_2$)(R$_2$), —N(R$_2$)C(O)(R$_2$), —C(O)OR$_2$, —C(O)N(R$_2$)(R$_2$), —SO$_2$N(R$_2$)(R$_2$), —N(R$_2$)SO$_2$-aryl, or —N(R$_2$)SO$_2$R$_2$;

R$_{1a}$ is hydrogen or C$_1$–C$_4$ alkyl;

R$_2$ is selected from the group consisting of: hydrogen, —C$_1$–C$_6$ alkyl, —C$_3$–C$_7$ cycloalkyl, and —CH$_2$-phenyl, wherein the alkyl or the cycloalkyl is unsubstituted or substituted with hydroxyl, C$_1$–C$_3$ alkoxy, thioalkyl, C(O)OR$_{2a}$, and wherein, if two —C$_1$–C$_6$ alkyl groups are present on one atom, the groups are optionally joined to form a C$_3$–C$_8$ cyclic ring optionally including oxygen, sulfur, or NR$_{2a}$, the C$_3$–C$_8$ cyclic ring being selected from the group consisting of pyrrolidine, piperidine, piperazine, morpholine, and thiomorpholine;

R$_{2a}$ is hydrogen or C$_1$–C$_6$ alkyl;

R$_4$ and R$_5$ are independently selected from the group consisting of: hydrogen, C$_1$–C$_6$ alkyl, substituted C$_1$–C$_6$ alkyl where the substituents are selected from: 1 to 5 halo, 1 to 3 hydroxy, 1 to 3 C$_1$–C$_{10}$ alkanoyloxy, 1 to 3 C$_1$–C$_6$ alkoxy, phenyl, phenoxy, 2-furyl, C$_1$–C$_6$ alkoxycarbonyl, and —S(O)$_m$(C$_1$–C$_6$ alkyl);

or wherein R$_4$ and R$_5$ are optionally taken together to form —(CH$_2$)$_r$L$_a$(CH$_2$)$_s$—, wherein L$_a$ is —C(R$_2$)$_2$—, —O—, —S(O)$_m$— or —N(R$_2$)—, wherein r and s are independently 1 to 3, and R$_2$ is defined above;

A is:

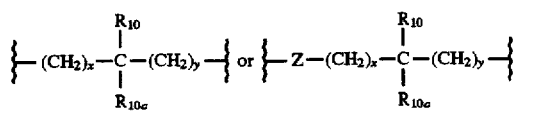

wherein x and y are independently 0, 1, 2 or 3;

Z is —N(R$_9$)— or —O—, wherein R$_9$ is hydrogen or C$_1$–C$_6$ alkyl;

R$_{10}$ and R$_{10a}$ are independently selected from the group consisting of: hydrogen, C$_1$–C$_6$ alkyl, trifluoromethyl, phenyl, and substituted C$_1$–C$_6$ alkyl wherein the substituents are selected from the group consisting of: imidazolyl, phenyl, indolyl, naphthyl, p-hydroxyphenyl, —OR$_2$, —S(O)$_m$R$_2$, —C(O)OR$_2$, —C$_3$–C$_7$ cycloalkyl, —N(R$_2$)(R$_2$), and —C(O)N(R$_2$)(R$_2$);

or R$_{10}$ and R$_{10a}$ are optionally independently joined to one or both of R$_4$ and R$_5$ groups to form an alkylene bridge between the terminal nitrogen and the alkyl portion of the R$_{10}$ or R$_{10a}$ groups, wherein the bridge contains 1 to 5 carbons atoms;

R$_8$ is hydrogen, C$_1$–C$_{10}$ alkyl, phenyl, benzyl or diphenyl methyl wherein the phenyl, benzyl or diphenyl groups may be substituted by halo, methyl or OR$_2$;

X is SO$_2$;

48

Y is selected from: SO$_2$, CO, C(O)O, C(O)N(R$_2$), and SO$_2$N(R$_2$);

m is 0, 1, or 2;

n is 1 or 2;

and pharmaceutically acceptable salts and individual diastereomers thereof.

2. The compound of claim 1 wherein:

R$_1$ is selected from the group consisting of: C$_1$–C$_{10}$ alkyl, aryl(C$_1$–C$_4$ alkyl)-, C$_5$–C$_6$ cycloalkyl-(C$_1$–C$_4$ alkyl)-, (C$_1$–C$_4$ alkyl)-K-C$_1$–C$_2$ alkyl-, aryl-K-(C$_1$–C$_2$ alkyl)-, aryl(C$_1$–C$_2$ alkyl)-K-(C$_1$–C$_2$ alkyl)-, C$_3$–C$_6$cycloalkyl-K-(C$_1$–C$_2$alkyl)-, C$_3$–C$_6$cycloalkyl(C$_1$–C$_2$alkyl)-K-(C$_1$–C$_2$alkyl)-, wherein K is O or S(O)$_m$, and the aryl is phenyl, or naphthyl and the heteroaryl is indolyl and the aryl and heteroaryl groups are unsubstituted or substituted by 1 to 2 C$_1$–C$_4$ alkyl, 1 to 2 halo, OR$_2$, C(O)OR$_2$, CF$_3$ or S(O)$_m$R$_2$;

R$_2$ is selected from the group consisting of: hydrogen, C$_1$–C$_6$ alkyl, C$_3$–C$_6$ cycloalkyl, wherein the alkyl or the cycloalkyl is unsubstituted or substituted with hydroxyl, C$_1$–C$_3$ alkoxy, thioalkyl, C(O)OR$_{2a}$, and, if two C$_1$–C$_6$ alkyls are present on one atom, they are optionally joined to form a C$_5$–C$_6$ cyclic ring optionally including the heteroatoms oxygen or NR$_{2a}$, the C$_3$–C$_8$ cyclic ring being selected from the group consisting of pyrrolidine, piperidine, piperazine, morpholine, thiomorpholine;

R$_{2a}$ is hydrogen or C$_1$–C$_4$ alkyl;

R$_4$ and R$_5$ are independently selected from the group consisting of: hydrogen, C$_1$–C$_4$ alkyl, substituted C$_1$–C$_4$ alkyl where the substituents may be 1 to 2 hydroxy or S(O)$_m$(C$_1$–C$_3$alkyl); or wherein R$_4$ and R$_5$ may be taken together to form (CH$_2$)$_r$N(R$_2$)(CH$_2$)$_s$, wherein r and s are independently 1 to 3 and R$_2$ is defined above;

A is:

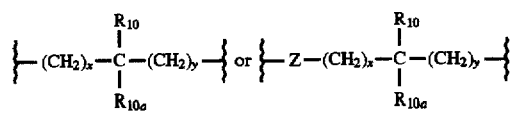

wherein x and y are independently 0, 1 or 2;

Z is —N(R$_9$)— or —O—, wherein R$_9$ is hydrogen or C$_1$–C$_4$ alkyl;

R$_{10}$ and R$_{10a}$ are independently selected from the group consisting of: hydrogen, C$_1$–C$_3$ alkyl; or R$_{10}$ and R$_{10a}$ are optionally independently joined to one or both of the R$_4$ and R$_5$ groups to form an alkylene bridge between the terminal nitrogen and the alkyl portion of the R$_{10}$ or R$_{10a}$ groups to form 5 or 6 membered rings containing the terminal nitrogen;

X is SO$_2$;

Y is CO, CO$_2$, or SO$_2$;

R$_8$ is C$_1$–C$_6$ alkyl, phenyl or benzyl optionally substituted with halo, methyl or OR$_2$;

m is 0, 1, or 2; and n is 1;

or their pharmaceutically acceptable salts and individual diastereomers thereof.

3. The compound of claim 1 of the structural formula V:

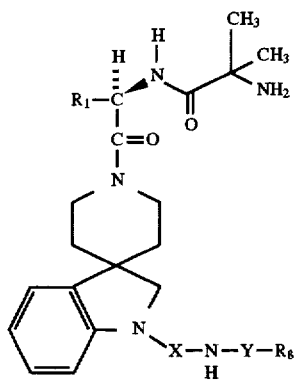

wherein:

$R_1$ is selected from the group consisting of:

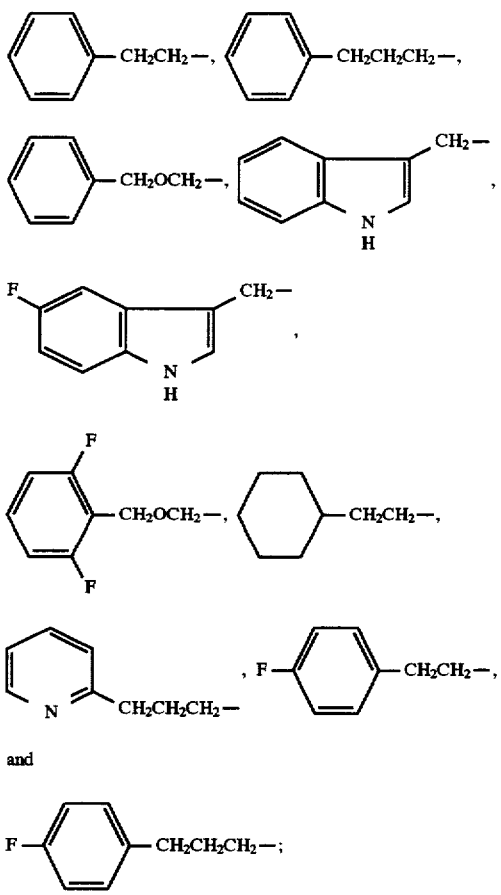

$R_2$ is selected from the group consisting of: hydrogen, $C_1$–$C_4$ alkyl;

$R_4$ and $R_5$ are independently selected from the group consisting of hydrogen, $C_1$–$C_4$ alkyl, substituted $C_1$–$C_4$ alkyl wherein the substituents are 1 to 2 hydroxy or wherein $R_4$ and $R_5$ maybe taken together to form piperazine;

A is

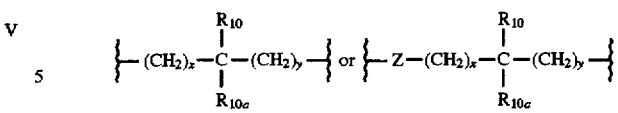

wherein x and y are independently 0, 1 or 2;

Z is $N(R_9)$ or —O—, wherein $R_9$ is hydrogen or methyl;

$R_{10}$ and $R_{10a}$ are independently selected from the group consisting of hydrogen and $C_1$–$C_3$ alkyl; or $R_{10}$ and $R_{10a}$ are optionally independently joined to one or both of the $R_4$ and $R_5$ group to form a pyrrolidine or piperidine ring;

X is $SO_2$;

Y is CO or $SO_2$;

$R_8$ is hydrogen, $C_1$–$C_4$ alkyl, phenyl or benzyl optionally substituted by halo, methyl or $OR_2$; and m is 0, 1, or 2;

and the pharmaceutically acceptable salts and individual diastereomers thereof.

4. A compound which is selected from the group consisting of:

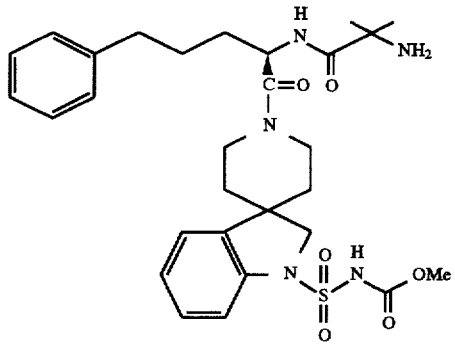

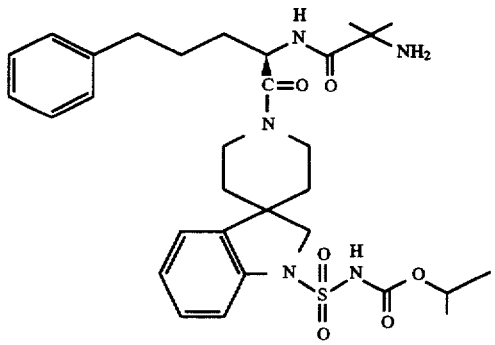

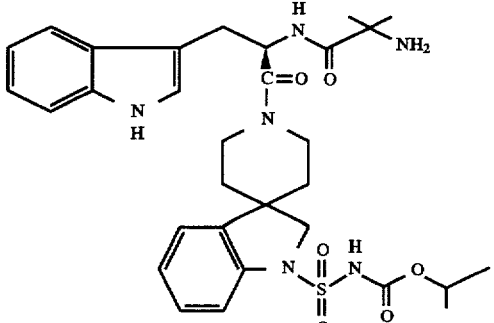

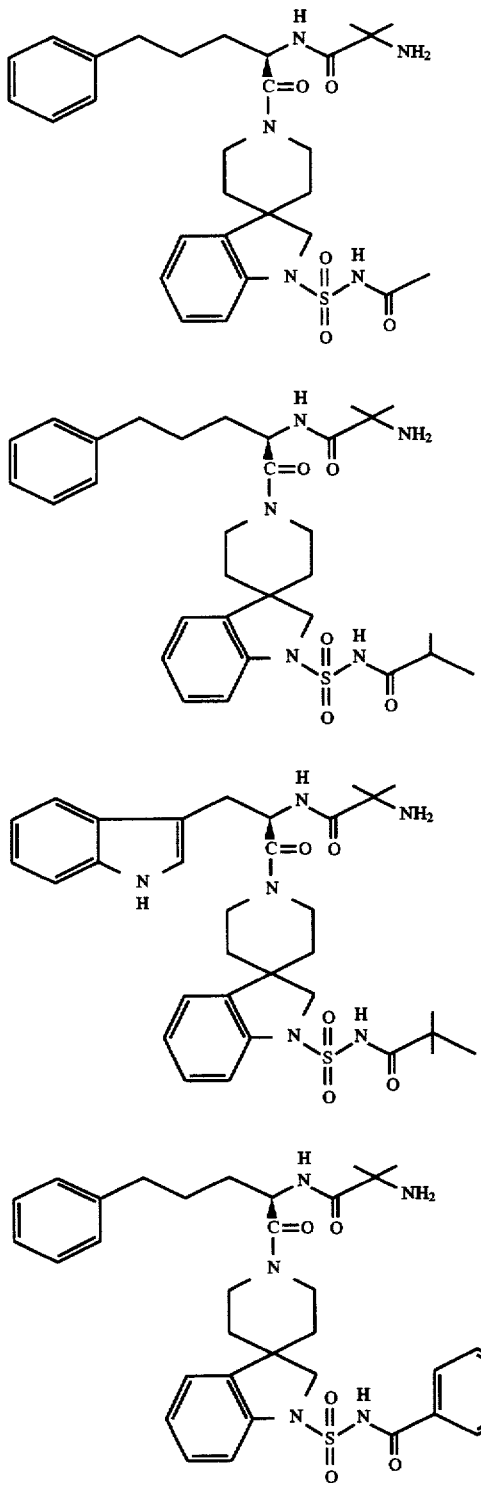

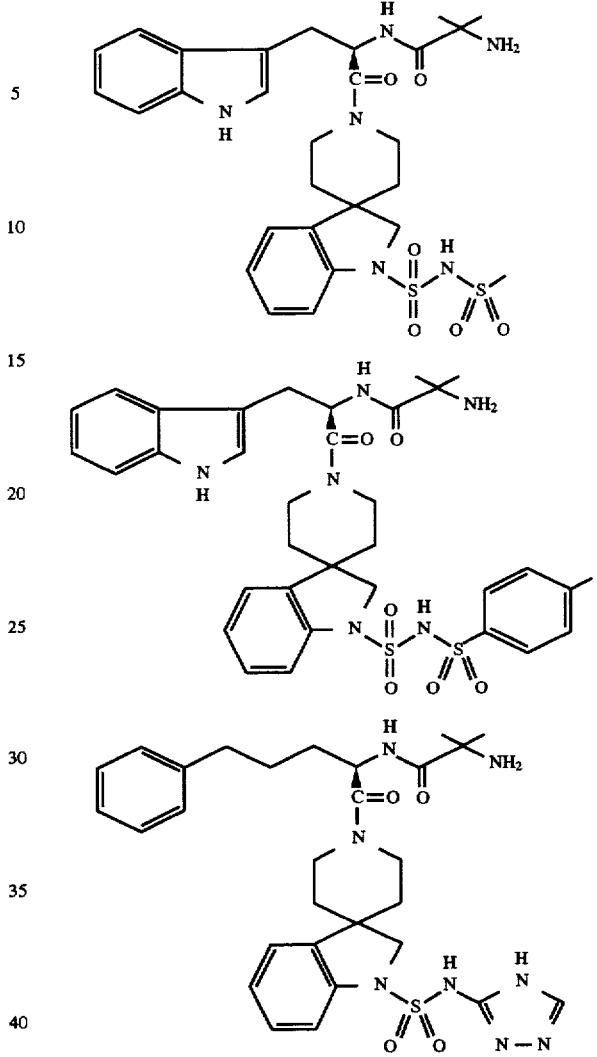

or a pharmaceutically acceptable salt thereof.

5. A pharmaceutical composition which comprises an inert carrier and a compound of claim 1.

6. A pharmaceutical composition which increases the endogenous production or release of growth hormone in a human or an animal which comprises an inert carrier and an effective amount of a compound of claim 1 in combination with an additional growth hormone secretagogue.

7. The pharmaceutical composition of claim 6 wherein the additional growth hormone secretagogue is selected from the group consisting of: growth hormone releasing factor; an analog of growth hormone releasing factor; IGF-1; and IGF-2.

8. A pharmaceutical composition for treating osteoporosis which comprises a combination of a bisphosphonate compound and a compound of claim 1.

9. The pharmaceutical composition of claim 8 wherein the bisphosphonate compound is alendronate.

10. A method for increasing levels of endogenous growth hormone in a human or an animal which comprises administering to such human or animal an effective amount of a compound of claim 1.

11. A method for increasing feed efficiency, promoting growth, increasing milk production and improving the carcass quality of livestock which comprises administering to such livestock an effective amount of a compound of claim 1.

12. A method for the treatment of a disease or a condition which is benefited by the anabolic effects of enhanced growth hormone levels that comprises administering to a patient in need thereof an effective amount a compound of claim 1.

13. The method of claim 12 wherein the disease or condition is selected from the group consisting of: osteoporosis; catabolic illness; immune deficiency, including that in individuals with a depressed $T_4/T_8$ cell ratio; hip fracture; musculoskeletal impairment in the elderly; growth hormone deficiency in adults or in children; obesity; cachexia and protein loss due to chronic illness such as AIDS or cancer; and the treatment of patients recovering from major surgery, wounds or burns.

14. A method for the treatment of osteoporosis which comprises administering to a patient with osteoporosis a combination of a bisphosphonate compound and a compound of claim 1.

15. The method of claim 14 wherein the bisphosphonate compound is alendronate.

16. A process for the preparation of a compound of claim 1 which comprises reacting a compound (1) of the formula:

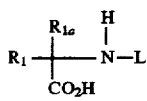

wherein L is an amino protecting group and wherein $R_1$ and $R_{1a}$ are as defined in claim 1, with a compound (2) of the formula:

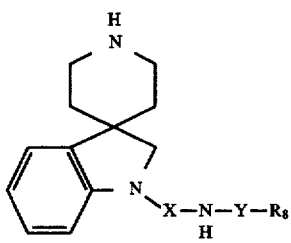

wherein $R_8$, X and Y are as defined in claim 1, to give a compound (3) of the formula:

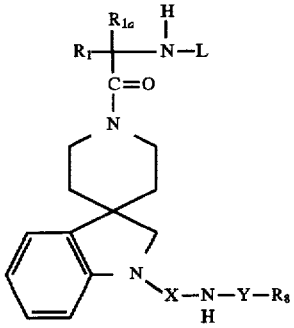

and thereafter removing the amino protecting group L; then reacting the product therefrom with an amino acid (5) or (6) of the formula:

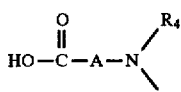

or

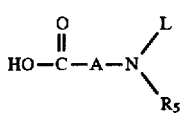

wherein L is an amino protecting group and wherein $R_4$, $R_5$, and A are as defined in claim 1, to give a compound (7) of the formula:

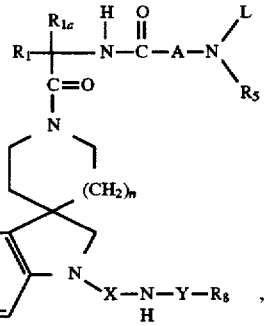

followed by removal of the amino protecting group L, if present, to give the compound of claim 1.

* * * * *